United States Patent
Bram et al.

(10) Patent No.: US 9,624,285 B2
(45) Date of Patent: Apr. 18, 2017

(54) METHODS OF TREATING DIABETES AND COMPOSITIONS CAPABLE OF SAME

(75) Inventors: Yaron Bram, Haifa (IL); Ehud Gazit, Ramat-HaSharon (IL)

(73) Assignee: Ramot a Tel-Aviv University Ltd., Tel-Aviv (IL)

( * ) Notice: Subject to any disclaimer, the term of this patent is extended or adjusted under 35 U.S.C. 154(b) by 2 days.

(21) Appl. No.: 13/700,444

(22) PCT Filed: Jun. 2, 2011

(86) PCT No.: PCT/IL2011/000436
§ 371 (c)(1),
(2), (4) Date: Nov. 28, 2012

(87) PCT Pub. No.: WO2011/151833
PCT Pub. Date: Dec. 8, 2011

(65) Prior Publication Data
US 2013/0071401 A1    Mar. 21, 2013

Related U.S. Application Data

(60) Provisional application No. 61/350,943, filed on Jun. 3, 2010.

(51) Int. Cl.
| | |
|---|---|
| *A61K 38/17* | (2006.01) |
| *C07K 14/575* | (2006.01) |
| *G01N 33/68* | (2006.01) |
| *C07K 16/26* | (2006.01) |

(52) U.S. Cl.
CPC ............ *C07K 14/575* (2013.01); *A61K 38/17* (2013.01); *C07K 16/26* (2013.01); *G01N 33/6893* (2013.01); *G01N 2333/4709* (2013.01); *G01N 2500/10* (2013.01)

(58) Field of Classification Search
CPC .............................. A61K 39/0005; A61K 38/17
See application file for complete search history.

(56) References Cited

U.S. PATENT DOCUMENTS

| | | | |
|---|---|---|---|
| 2009/0246191 A1 | 10/2009 | O'Nuallain et al. | |
| 2009/0285822 A1* | 11/2009 | Schenk .............. | A61K 39/0007 424/139.1 |
| 2013/0071401 A1 | 3/2013 | Bram et al. | |

FOREIGN PATENT DOCUMENTS

| | | | | |
|---|---|---|---|---|
| WO | WO 03092619 A2 * | 11/2003 | ......... | A61K 39/0008 |
| WO | WO 2004/024090 | 3/2004 | | |
| WO | WO 2006004824 A1 * | 1/2006 | ............ | B01D 15/34 |
| WO | WO 2007062852 A2 * | 6/2007 | | |
| WO | WO 2009048631 A1 * | 4/2009 | | |
| WO | WO 2010/054127 | 5/2010 | | |
| WO | WO 2011/151833 | 12/2011 | | |

OTHER PUBLICATIONS

Kayed et al. (2003) Science, 300:486-489.*
Liu et al. (2010) J. Am. Chem. Soc. 132:18223-18232.*
Meier et al. (2006) Am. J. Physiol. Endocrinol. Metab. 291:E1317-E1324.*
Suh et al. (2008) J. Biol. Inorg. Chem. 13:693-701.*
Zraika et al. (2010) Toxic oligomers and islet beta cell death: guilty by association or convicted by circumstantial evidence? Diabetologia, 53:1049-1056, Epub: Feb. 25, 2010.*
Patil SM et al. (May 1, 2009) Dynamic alpha-helix structure of micelle-bound human amylin. J. Biol. Chem. 284(18):11982-11991.*
Quist A et al. (2005) Amyloid ion channels: A common structural link for protein-misfolding disease. Proc. Natl. Acad. Sci. USA, 102(30):10427-10432.*
Barghorn S et al. (2005) Globular amyloid beta-peptide 1-42 oligomer—a homogenous and stable neuropathological protein in Alzheimer's disease. J. Neurochem. 95:834-847.*
Green JD et al. (2004) Human amylin oligomer growth and fibril elongation define two distinct phases in amyloid formation. J. Biol. Chem. 279(13):12206-12212.*
Wiltzius JJW et al. Atomic structures of IAPP (amylin) fusions suggest a mechanism for fibrillation and the role of insulin in the process. Protein Sci. (2009) 18:1521-1530.*
International Preliminary Report on Patentability Dated Dec. 13, 2012 From the International Bureau of WIPO Re. Application No. PCT/IL2011/000436.
International Search Report and the Written Opinion Dated Oct. 6, 2011 From the International Searching Authority Re. Application No. PCT/IL2011/000436.
Matveyenko et al. "Islet Amyloid Polypeptide (IAPP) Transgenic Rodents as Models for Type 2 Diabetes", ILAR Journal, XP009151943, 47(3): 225-233, Jan. 1, 2006. Abstract, p. 231, Right Col., Summary.
Porat et al. "The Human Islet Amyloid Polypeptide Forms Transient Membrane-Active Prefibrillar Assemblies", Biochemistry, 42: 10971-10977, 2003.
Ritzel et al. "Human Islet Amyloid Polypeptide Oligomers Disrupt Cell Coupling, Induce Apoptosis, and Impair Insulin Secretion in Isolated Human Islets", Diabetes, XP009151944, 56(1): 65-71, Jan. 1, 2007. Abstract, p. 70, Last Para, r-h Col.

* cited by examiner

*Primary Examiner* — Kimberly A. Ballard

(57) ABSTRACT

A composition of matter is disclosed which comprises isolated oligomers of human islet amyloid polypeptide (IAPP). Antibodies recognizing same are also disclosed. Use of the composition of matter and the antibodies are also disclosed.

7 Claims, 5 Drawing Sheets
(5 of 5 Drawing Sheet(s) Filed in Color)

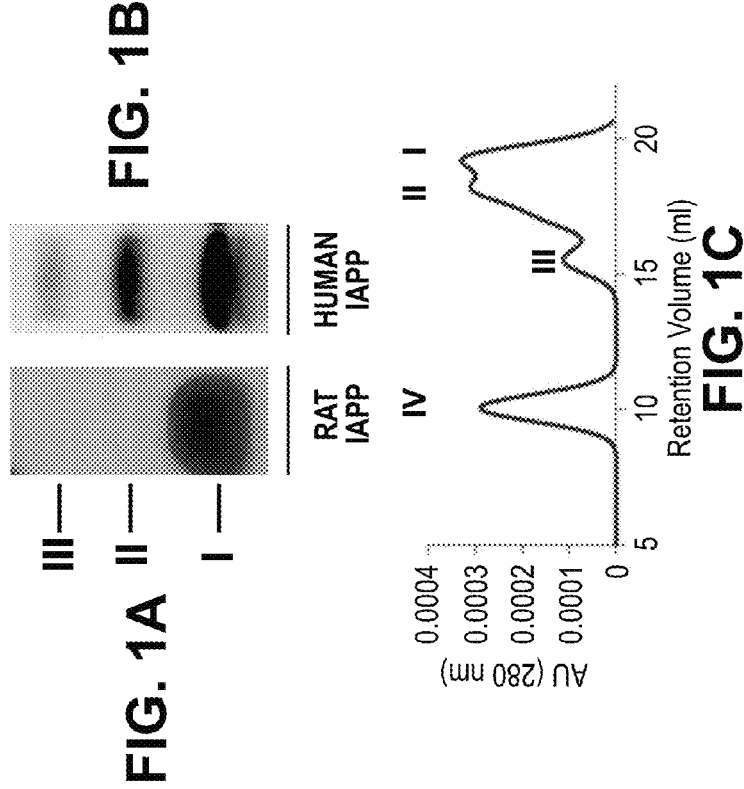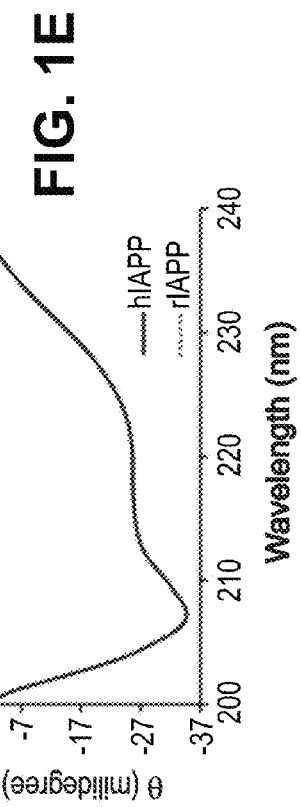

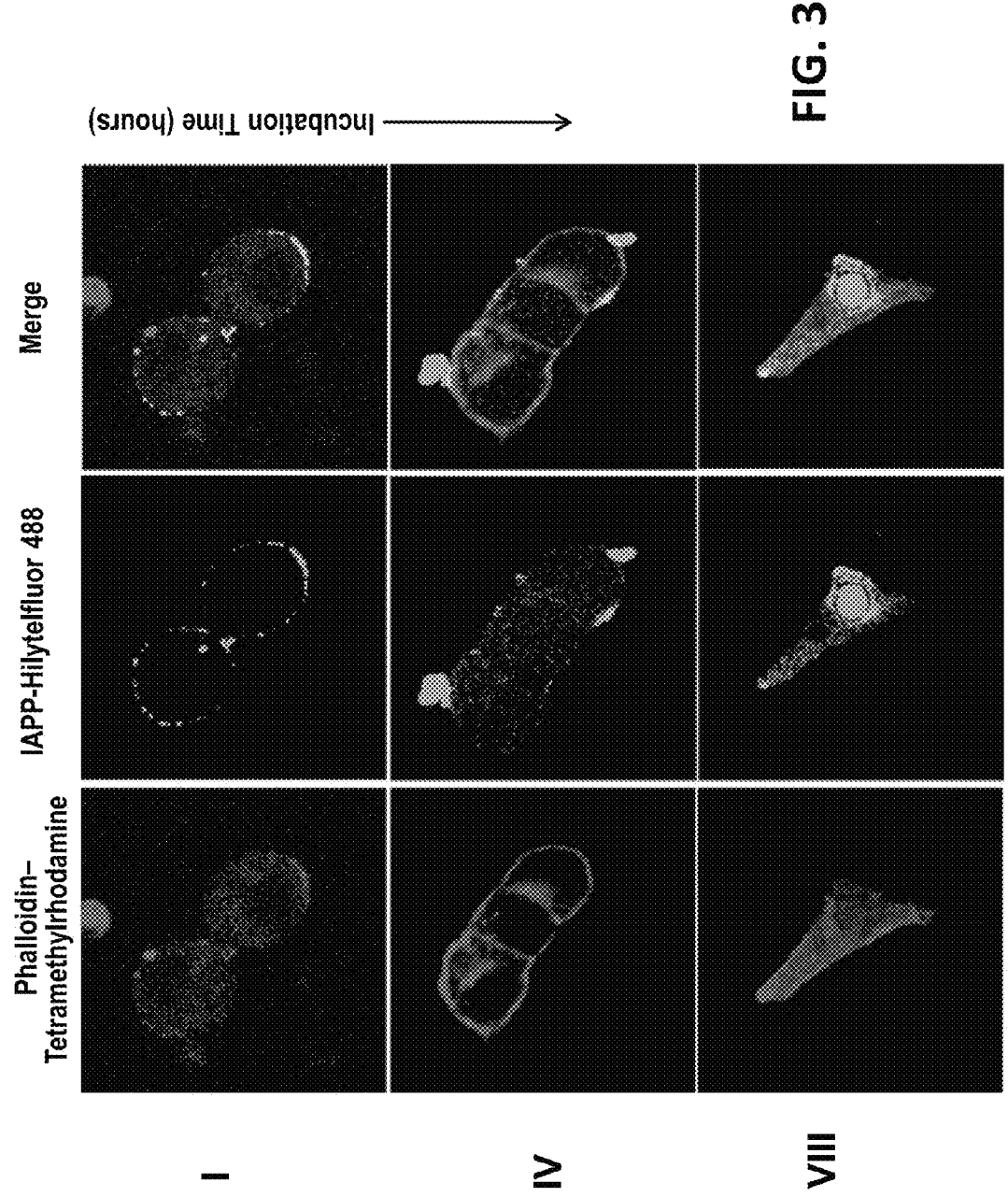

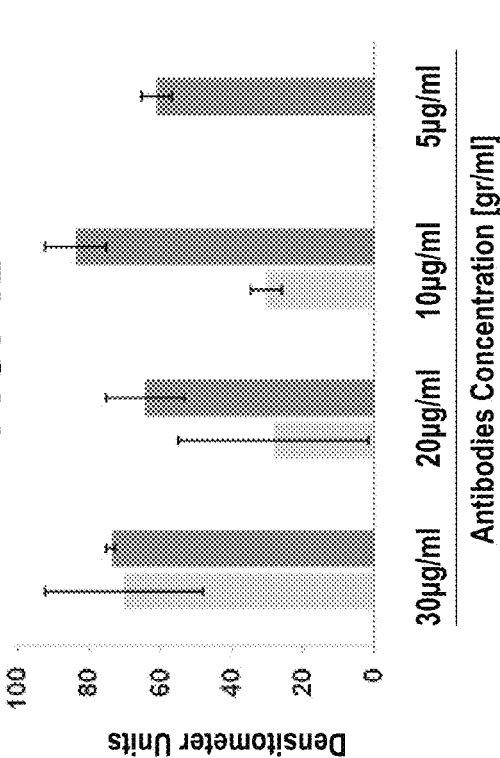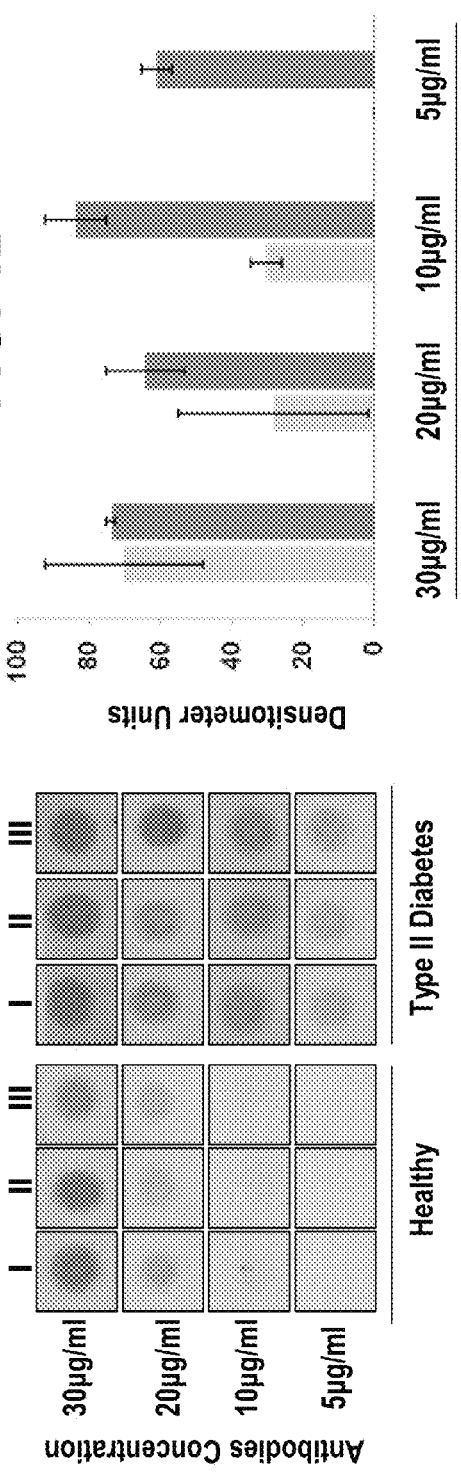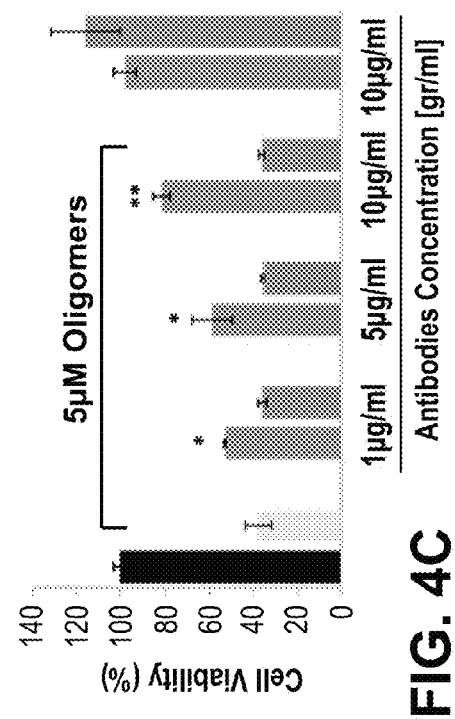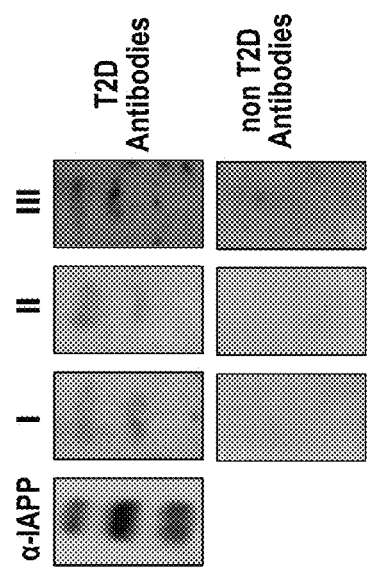

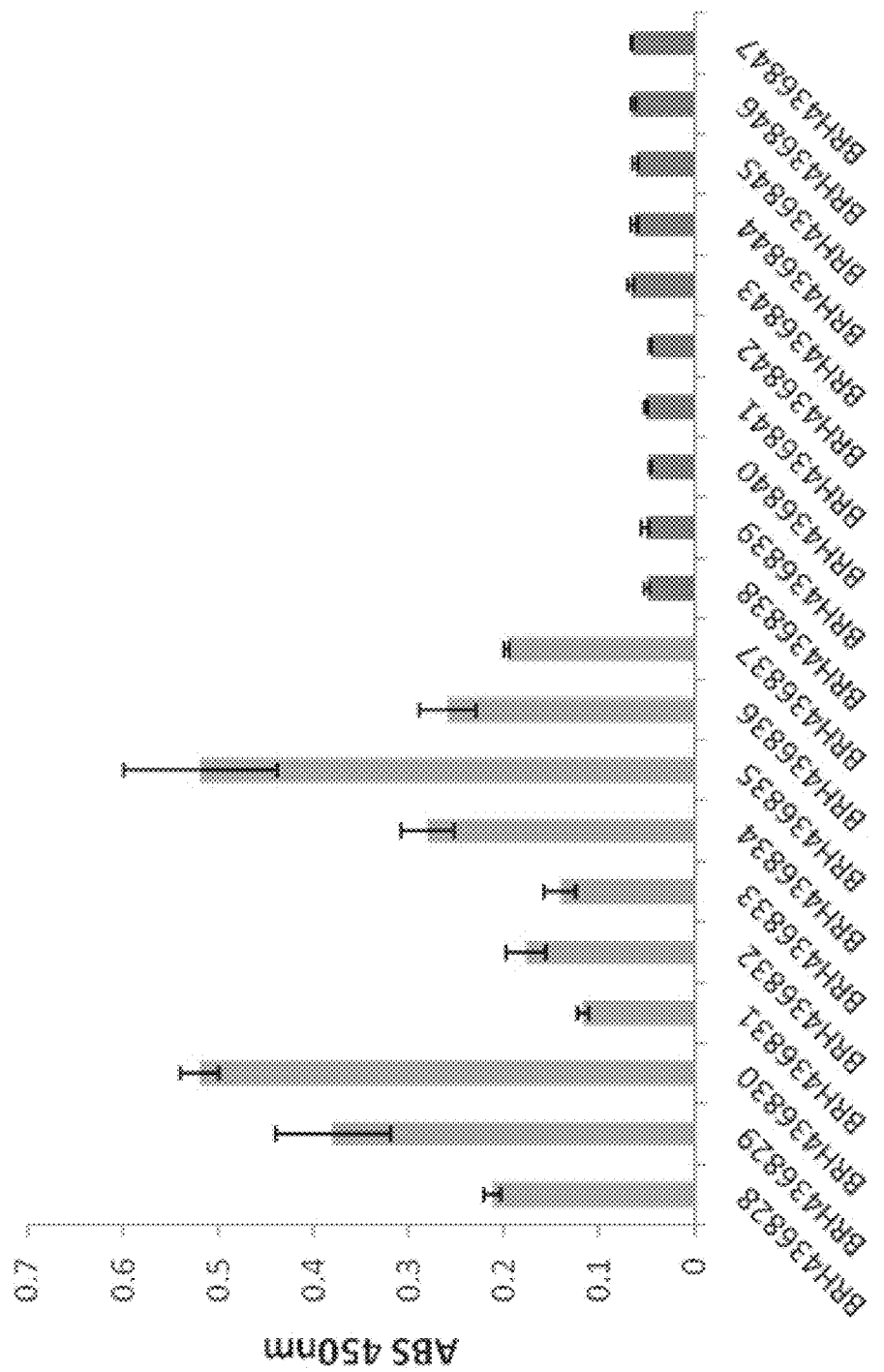

SEQUENCE LISTING

```
<160> NUMBER OF SEQ ID NOS: 19

<210> SEQ ID NO 1
<211> LENGTH: 1992
<212> TYPE: DNA
<213> ORGANISM: Homo sapiens

<400> SEQUENCE: 1
gggtatataa gagctggatt actagttagc aaatgagggg gtaaatattc cagtggatac      60
aagcttggac tcttttcttg aagctttctt tctatcagaa gcatttgctg atattgctga     120
cattgaaaca ttaaaagaaa atttgagaag caatgggcat cctgaagctg caagtatttc     180
tcattgtgct ctctgttgca ttgaaccatc tgaaagctac acccattgaa agtcatcagg     240
tggaaaagcg gaaatgcaac actgccacat gtgcaacgca gcgcctggca aattttttag     300
ttcattccag caacaacttt ggtgccattc tctcatctac caacgtggga tccaatacat     360
atggcaagag gaatgcagta gaggttttaa agagagagcc actgaattac ttgccccttt     420
agaggacaat gtaactctat agttattgtt ttatgttcta gtgatttcct gtataattta     480
```

```
acagtgccct tttcatctcc agtgtgaata tatggtctgt gtgtctgatg tttgttgcta      540
ggacatatac cttctcaaaa gattgtttta tatgtagtac taactaaggt cccataataa      600
aaagatagta tcttttaaaa tgaaatgttt ttgctataga tttgtatttt aaaacataag      660
aacgtcattt tgggacctat atctcagtgg cacaggttta agaacgaagg agaaaaaggt      720
agtttgaacc ttggtaaatt gtaaacagct aataatgaag ttattcttga catgagaaaa      780
tcagtaattg gaccaggcgc ggtggctctt gcctgtaatc ccagcacttt gggaggccga      840
ggcaggcaga tcacaaggtc aggagttcga gaccagcctg accaacatgg tgaaaccctg      900
tctctactaa aaatacaaaa attagccggg ggtggtgaca tgtgcctgta atcccagcta      960
ctcaggaggc taaggcagga gaatcgctta acccaggag gcggaggttg cagtgagccg      1020
agattgcacc actgcactcc agcctgggtg gcagagtgag actcgtctca aaaaaaagaa      1080
agaaaattag taattgtaag taccccctgat aagcaaatta gtaattgtca ataccctgt      1140 taagcaattc ctttttgcag tatatttctg aaatgacaga atgctgtttt aaaaacaaag      1200
aaataaaatc ctgctcctga ctcggtcaaa atattttta aagtctattg tttgttgtgc      1260
ttgctggtac taagaggcta tttaaaagta taaaactgct ttgtatccat gagggtttca      1320
ttgtgtgtta gcagcagtga gcttctatta aatgtatatg tcatttattt tgtttaagtg      1380
gctttcagca aacctcagtc atattcttat gcagggtatt gcgaaacaac ttgtgttcta      1440
ttaatcgtgt cttcaattaa aagaccacag acttctggaa actctttgct gtataagaat      1500
tatttctttt gtttaacaaa ttagacattt ctggcagagg ttatgtatat gatacacttt      1560
ttttgatagc agctgcaatg ttggacagaa gatgaaatgc tttgctttga gtcagattct      1620
tatgaatatc tgcttttccc tgactttgag ttaggtagct ttggaagtag cattaattca      1680
gataaactgc catcatgctg cgttatgcca tttctaaaga cactcaactt gtacttttaa      1740
aaaaatagaa aaaataagca tttcaatcta agtggaaatt tgactcattg acttacattt      1800
ctaagttaaa atttcccttt atgaagtgtg ccttaggtta ccaaattgta gaggctttcg      1860
ttggtggtgg taagtggtag cggtagtgag tgtatagagg cagggaaata tatttataat      1920
aaattctatg tcatgaatta catattgaaa taaataggtg aatatacaaa tttataaaaa      1980
aaaaaaaaaa aa                                                          1992
```

<210> SEQ ID NO 2
<211> LENGTH: 89
<212> TYPE: PRT
<213> ORGANISM: Homo sapiens

<400> SEQUENCE: 2

```
Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala Thr Cys Ala Thr Gln Arg Leu Ala Asn Phe
        35                  40                  45

Leu Val His Ser Ser Asn Asn Phe Gly Ala Ile Leu Ser Ser Thr Asn
    50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85
```

```
<210> SEQ ID NO 3
<211> LENGTH: 725
<212> TYPE: DNA
<213> ORGANISM: Mus musculus

<400> SEQUENCE: 3
gtcgtgcatg cagacttggg ctgtagttcc tgaagcttca ggctgtcaaa gcattttctg      60
atattgctgc ctcggaccac tgaaagggat cttgagaaat gatgtgcatc tccaaactgc     120
cagctgtcct cctcatcctc tctgtggcac tgaaccactt gagagctaca cctgtcagaa     180
gtggtagcaa ccctcagatg acaaacgga agtgcaacac ggccacgtgt gccacacaac      240
gcctggcaaa cttttggtt cgttccagca acaaccttgg tccagtcctc ccaccaacca      300
acgtgggatc gaatacatat ggcaagagga atgcggcagg ggatccaaat agggaatcct     360
tggatttctt actcgtttaa agtcaatgta cttctgcagc acttaatact ttatgtgtaa     420
atgctctggt gatttcctga atattaacag tacctttttc attccccct cagtgagaat      480 gcacaatgtg cttgtgcttg atgactgtgt gtgtaaattc tcatgctaag aattgcttta     540
aactgagtat tgatcaagtt cagagtgaag tcaatgtctc taatcacaca tgttcttgct     600
atacatttat attttaggga cacttaaaat ttctgttttt accttgtacc tctatgactc     660
aagtttaaca ataagaaga ccatgggatg atgaaaaaaa aaaaaaaaa aaaaaaaaa        720 aaaaa                                                                 725

<210> SEQ ID NO 4
<211> LENGTH: 93
<212> TYPE: PRT
<213> ORGANISM: Mus musculus

<400> SEQUENCE: 4

Met Met Cys Ile Ser Lys Leu Pro Ala Val Leu Leu Ile Leu Ser Val
1               5                   10                  15

Ala Leu Asn His Leu Arg Ala Thr Pro Val Arg Ser Gly Ser Asn Pro
            20                  25                  30

Gln Met Asp Lys Arg Lys Cys Asn Thr Ala Thr Cys Ala Thr Gln Arg
        35                  40                  45

Leu Ala Asn Phe Leu Val Arg Ser Ser Asn Asn Leu Gly Pro Val Leu
    50                  55                  60

Pro Pro Thr Asn Val Gly Ser Asn Thr Tyr Gly Lys Arg Asn Ala Ala
65                  70                  75                  80

Gly Asp Pro Asn Arg Glu Ser Leu Asp Phe Leu Leu Val
                85                  90

<210> SEQ ID NO 5
<211> LENGTH: 238
<212> TYPE: PRT
<213> ORGANISM: Aequorea macrodactyla

<400> SEQUENCE: 5

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60
```

Gly Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Leu Gln Thr Ala Ile Ser
        195                 200                 205

Lys Asp Arg Asn Glu Thr Arg Asp His Met Val Phe Leu Glu Phe Phe
    210                 215                 220

Ser Ala Cys Gly His Thr His Gly Met Asp Glu Leu Tyr Lys
225                 230                 235

<210> SEQ ID NO 6
<211> LENGTH: 717
<212> TYPE: DNA
<213> ORGANISM: aequorea macrodactyla

<400> SEQUENCE: 6
atgagtaaag gagaagaact tttcactggg attgtcccag ttctcattga gttagacggt        60
gatgtccatg gacataaatt ctctgtcaga ggagaagggg aaggcgatgc agattatgga       120
aaacttgaaa tcaaattcat ttgcactact ggaaagctac cagttccatg ccaacactt        180 gttactacac tgggctacgg catccaatgt ttcgcaagat acccagaaca catgaaaatg       240
aatgacttct tcaagagtgc catgcctgag ggttacattc aagaagaac catcttttc        300 caagatgatg gaaaatacaa gacacgtggt gaagtcaagt tgaaggtga tactcttgtt       360 aacagaattg agctcaaagg tatggacttt aagaagatg gcaatatcct tggacacaag       420
ttggagtaca atttaattc acataatgta tacattatgc cggacaaagc caataatgga       480
ctcaaagtca atttcaaaat tagacacaat atcgaaggtg gtggtgtcca acttgctgat       540
cattaccaaa caaatgttcc ccttggagac ggtcctgtcc ttataccaat caatcactac       600
ctatccttgc aaacagccat ttcaaaagat cgaaatgaga cgagagatca tatggtgttt       660
ctggaatttt tctcagcttg tggacataca catggcatgg atgaactata caaataa          717

<210> SEQ ID NO 7
<211> LENGTH: 489
<212> TYPE: PRT
<213> ORGANISM: Artificial sequence
<220> FEATURE:
<223> OTHER INFORMATION: Alkaline phosphatase

```
<400> SEQUENCE: 7

Met Lys Gln Ser Thr Ile Ala Leu Ala Leu Leu Pro Leu Leu Phe Thr
 1               5                  10                  15

Pro Val Thr Lys Ala Arg Thr Pro Glu Met Pro Leu Gln Gly Thr Ala
            20                  25                  30

Val Asp Gly Gly Gly Ser Met His Ala Ser Leu Glu Val Leu Glu
        35                  40                  45

Asn Arg Ala Ala Gln Gly Asp Ile Thr Ala Pro Gly Gly Ala Arg Arg
        50                  55                  60

Leu Thr Gly Asp Gln Thr Ala Ala Leu Arg Asp Ser Leu Ser Asp Lys
65                  70                  75                  80

Pro Ala Lys Asn Ile Ile Leu Leu Ile Gly Asp Gly Met Gly Asp Ser
                85                  90                  95

Glu Ile Thr Ala Ala Arg Asn Tyr Ala Glu Gly Ala Gly Gly Phe Phe
            100                 105                 110

Lys Gly Ile Asp Ala Leu Pro Leu Thr Gly Gln Tyr Thr His Tyr Ala
            115                 120                 125

Leu Asn Lys Lys Thr Gly Lys Pro Asp Tyr Val Thr Asp Ser Ala Ala
        130                 135                 140

Ser Ala Thr Ala Trp Ser Thr Gly Val Lys Thr Tyr Asn Gly Ala Leu
145                 150                 155                 160

Gly Val Asp Ile His Glu Lys Asp His Pro Thr Ile Leu Glu Met Ala
                165                 170                 175

Lys Ala Ala Gly Leu Ala Thr Gly Asn Val Ser Thr Ala Glu Leu Gln
            180                 185                 190

Asp Ala Thr Pro Ala Ala Leu Val Ala His Val Thr Ser Arg Lys Cys
        195                 200                 205

Tyr Gly Pro Ser Ala Thr Ser Glu Lys Cys Pro Gly Asn Ala Leu Glu
    210                 215                 220

Lys Gly Gly Lys Gly Ser Ile Thr Glu Gln Leu Leu Asn Ala Arg Ala
225                 230                 235                 240

Asp Val Thr Leu Gly Gly Gly Ala Lys Thr Phe Ala Glu Thr Ala Thr
                245                 250                 255

Ala Gly Glu Trp Gln Gly Lys Thr Leu Arg Glu Gln Ala Gln Ala Arg
            260                 265                 270

Gly Tyr Gln Leu Val Ser Asp Ala Ala Ser Leu Asn Ser Val Thr Glu
        275                 280                 285

Ala Asn Gln Gln Lys Pro Leu Leu Gly Leu Phe Ala Asp Gly Asn Met
    290                 295                 300

Pro Val Arg Trp Leu Gly Pro Lys Ala Thr Tyr His Gly Asn Ile Asp
305                 310                 315                 320

Lys Pro Ala Val Thr Cys Thr Pro Asn Pro Gln Arg Asn Asp Ser Val
                325                 330                 335

Pro Thr Leu Ala Gln Met Thr Asp Lys Ala Ile Glu Leu Leu Ser Lys
            340                 345                 350

Asn Glu Lys Gly Phe Phe Leu Gln Val Glu Gly Ala Ser Ile Asp Lys
        355                 360                 365

Gln Asp His Ala Ala Asn Pro Cys Gly Gln Ile Gly Glu Thr Val Asp
    370                 375                 380

Leu Asp Glu Ala Val Gln Arg Ala Leu Glu Phe Ala Lys Lys Glu Gly
385                 390                 395                 400
```

```
Asn Thr Leu Val Ile Val Thr Ala Asp His Ala Ser Gln Ile
                405                 410                 415

Val Ala Pro Asp Thr Lys Ala Pro Gly Leu Thr Gln Ala Leu Asn Thr
            420                 425                 430

Lys Asp Gly Ala Val Met Val Met Ser Tyr Gly Asn Ser Glu Glu Asp
        435                 440                 445

Ser Gln Glu His Thr Gly Ser Gln Leu Arg Ile Ala Ala Tyr Gly Pro
    450                 455                 460

His Ala Ala Asn Val Val Gly Leu Thr Asp Gln Thr Asp Leu Phe Tyr
465                 470                 475                 480

Thr Met Lys Ala Ala Leu Gly Leu Lys
                485
```

<210> SEQ ID NO 8
<211> LENGTH: 1470
<212> TYPE: DNA
<213> ORGANISM: Artificial sequence
<220> FEATURE:
<223> OTHER INFORMATION: Alkaline phosphatase coding sequence

<400> SEQUENCE: 8

```
ttatttcagc cccagagcgg ctttcatggt gtagaagaga tcggtctggt cggtcagtcc      60
aacaacattg gcggcatgcg ggccatacgc cgcaatacgc aactgactgc cggtatgttc     120
ttgtgaatcc tcttcggagt tcccgtaact catcaccatc actgcgccat ctttggtatt     180
tagcgcctgg gtgaggcccg gagctttggt atccggcgca caatctggc tggcgtgggc     240
gtgatcagcg gtgactatga ccagcgtgtt accctccttt ttagcgaatt ccagcgcccg     300
ttgtacggct tcatcgagat cgaccgtctc gccaatttgc cacaaggat cgcagcatg     360
atcctgttta tcgattgacg caccttcaac ttgcaggaaa aagcctttct catttttact     420
caacaattca atggctttgt cggtcatctg cgccagggtt ggtacactgt cattacgttg     480
cggatttggc gtacaggtga ctgcgggctt atcgatattg ccatggtacg ttgctttcgg     540
tcctagccag cgcactggca tattgccgtc agcaaacagg ccaagcaggg gttttttgctg     600
attcgcttcc gtcaccgaat tcagtgaggc agcatcgctc accaactgat aaccacgcgc     660
ctgtgcctgt tcacgcagcg ttttttccctg ccattcacca gcggttgccg tttcagcaaa     720
ggttttgcg ccgccgccaa gcgtaacgtc ggcacgagcg ttaagcagct gttcggtaat     780
cgatcctttt ccgcctttt ccagagcgtt acccggacat ttttcactgg tcgcgctcgg     840
accgtagcat ttgcgcgagg tcacatgtgc caccagcgca gcgggcgtgg catcctgcaa     900
ctctgcggta gaaacgttac cggtcgccag acctgcggct tttgccattt ccagaatcgt     960
tgggtgatct ttttcgtgaa tatcgacgcc cagcgcgccg ttataggttt tgacaccggt    1020
tgaccaggcg gttgctgatg cagccgagtc ggtgacgtag tccggtttgc cggttttttt    1080
attcagcgca tagtgagtgt attgcccggt aagcggtaag gcatctatac ctttaaaaaa    1140
gccgcccgca ccttcggcat aattacgtgc ggcagtaatt tccgagtccc ccatcccatc    1200
gccaatcagc aaaataatat tttttgcagg tttatcgcta agagaatcac gcagagcggc    1260
agtctgatca cccgttaaac ggcgagcacc gccgggtgca gtaatatcgc cctgagcagc    1320
ccggttttcc agaacctcga ggctagcatg catagaaccg ccaccaccgt cgacagcggt    1380
accctgcaga ggcatttctg gtgtccgggc ttttgtcaca ggggtaaaca gtaacggtaa    1440
gagtgccagt gcaatagtgc tttgtttcac                                     1470
```

```
<210> SEQ ID NO 9
<211> LENGTH: 309
<212> TYPE: PRT
<213> ORGANISM: Artificial sequence
<220> FEATURE:
<223> OTHER INFORMATION: Peroxidase

<400> SEQUENCE: 9

Met Gln Leu Thr Pro Thr Phe Tyr Asp Asn Ser Cys Pro Asn Val Ser
1               5                   10                  15

Asn Ile Val Arg Asp Thr Ile Val Glu Leu Arg Ser Asp Pro Arg
            20                  25                  30

Ile Ala Ala Ser Ile Leu Arg Leu His Phe His Asp Cys Phe Val Asn
            35                  40                  45

Gly Cys Asp Ala Ser Ile Leu Leu Asp Asn Thr Thr Ser Phe Arg Thr
    50                  55                  60

Glu Lys Asp Ala Phe Gly Asn Ala Asn Ser Ala Arg Gly Phe Pro Val
65                  70                  75                  80

Ile Asp Arg Met Lys Ala Ala Val Glu Ser Ala Cys Pro Arg Thr Val
                85                  90                  95

Ser Cys Ala Asp Leu Leu Thr Ile Ala Ala Gln Gln Ser Val Thr Leu
            100                 105                 110

Ala Gly Gly Pro Ser Trp Arg Val Pro Leu Gly Arg Arg Asp Ser Leu
            115                 120                 125

Gln Ala Phe Leu Asp Leu Ala Asn Ala Asn Leu Pro Ala Pro Phe Phe
    130                 135                 140

Thr Leu Pro Gln Leu Lys Asp Ser Phe Arg Asn Val Gly Leu Asn Arg
145                 150                 155                 160

Ser Ser Asp Leu Val Ala Leu Ser Gly Gly His Thr Phe Gly Lys Asn
                165                 170                 175

Gln Cys Arg Phe Ile Met Asp Arg Leu Tyr Asn Phe Ser Asn Thr Gly
            180                 185                 190

Leu Pro Asp Pro Thr Leu Asn Thr Thr Tyr Leu Gln Thr Leu Arg Gly
            195                 200                 205

Leu Cys Pro Leu Asn Gly Asn Leu Ser Ala Leu Val Asp Phe Asp Leu
    210                 215                 220

Arg Thr Pro Thr Ile Phe Asp Asn Lys Tyr Tyr Val Asn Leu Glu Glu
225                 230                 235                 240

Gln Lys Gly Leu Ile Gln Ser Asp Gln Glu Leu Phe Ser Ser Pro Asn
                245                 250                 255

Ala Thr Asp Thr Ile Pro Leu Val Arg Ser Phe Ala Asn Ser Thr Gln
            260                 265                 270

Thr Phe Phe Asn Ala Phe Val Glu Ala Met Asp Arg Met Gly Asn Ile
            275                 280                 285

Thr Pro Leu Thr Gly Thr Gln Gly Gln Ile Arg Leu Asn Cys Arg Val
    290                 295                 300

Val Asn Ser Asn Ser
305

<210> SEQ ID NO 10
<211> LENGTH: 955
<212> TYPE: DNA
<213> ORGANISM: Artificial sequence
<220> FEATURE:
<223> OTHER INFORMATION: Peroxidase coding sequence
```

<400> SEQUENCE: 10

```
aagcttaacc atgcagttaa ccccctacatt ctacgacaat agctgtccca acgtgtccaa    60
catcgttcgc gacacaatcg tcaacgagct cagatccgat cccaggatcg ctgcttcaat   120
attacgtctg cacttccatg actgcttcgt gaatggttgc gacgctagca tattactgga   180
caacaccacc agtttccgca ctgaaaagga tgcattcggg aacgctaaca gcgccagggg   240
ctttccagtg atcgatcgca tgaaggctgc cgttgagtca gcatgcccac gaacagtcag   300
ttgtgcagac ctgctgacta tagctgcgca acagagcgtg actcttgcag gcggaccgtc   360
ctggagagtg ccgctcggtc gacgtgactc cctacaggca ttcctagatc tggccaacgc   420
caacttgcct gctccattct tcaccctgcc ccagctgaag gatagcttta gaaacgtggg   480
tctgaatcgc tcgagtgacc ttgtggctct gtccggagga cacacatttg aaagaaccca   540
gtgtaggttc atcatggata ggctctacaa tttcagcaac actgggttac ctgaccccac   600
gctgaacact acgtatctcc agacactgag aggcttgtgc ccactgaatg caacctcag   660
tgcactagtg gactttgatc tgcggacccc aaccatcttc gataacaagt actatgtgaa   720
tctagaggag cagaaaggcc tgatacagag tgatcaagaa ctgtttagca gtccaaacgc   780
cactgacacc atcccactgg tgagaagttt tgctaactct actcaaacct tctttaacgc   840
cttcgtggaa gccatggacc gtatgggtaa cattacccct ctgacgggta cccaaggcca   900
gattcgtctg aactgcagag tggtcaacag caactcttaa taaggatccg aattc         955
```

<210> SEQ ID NO 11
<211> LENGTH: 286
<212> TYPE: PRT
<213> ORGANISM: Artificial sequence
<220> FEATURE:
<223> OTHER INFORMATION: Synthetic construct translated protein product

<400> SEQUENCE: 11

```
Gln Ser Val Leu Thr Gln Pro Pro Ser Val Ser Gly Ser Pro Gly Gln
1               5                   10                  15

Ser Ile Thr Ile Ser Cys Thr Gly Thr Ser Ser Asp Ile Gly Thr Tyr
            20                  25                  30

Lys Ile Val Ser Trp Tyr Gln Gln His Pro Gly Lys Ala Pro Lys Leu
        35                  40                  45

Met Ile Tyr Asp Val Asn Gln Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Gly
                85                  90                  95

Ser Thr Leu Val Phe Gly Gly Gly Thr Lys Leu Thr Val Leu Gly Ser
            100                 105                 110

Ser Gly Gly Gly Gly Ser Gly Gly Gly Ser Gly Gly Ser Ala Leu
        115                 120                 125

Gln Val Gln Leu Gln Gln Ser Gly Ala Glu Val Lys Lys Pro Gly Glu
    130                 135                 140

Ser Leu Lys Ile Ser Cys Lys Gly Ser Gly Tyr Ser Phe Thr Ser Tyr
145                 150                 155                 160

Trp Ile Gly Trp Val Arg Gln Met Pro Gly Lys Gly Leu Glu Trp Met
                165                 170                 175

Gly Ile Ile Tyr Pro Gly Asp Ser Asp Thr Arg Tyr Ser Pro Ser Phe
            180                 185                 190
```

```
Gln Gly Gln Val Thr Ile Ser Ala Asp Lys Ser Ile Ser Thr Ala Tyr
            195                 200                 205
Leu Gln Trp Ser Ser Leu Lys Ala Ser Asp Thr Ala Met Tyr Tyr Cys
        210                 215                 220
Ala Arg His Arg Ala Ala Ser Gly Ser Pro Asp Ala Cys Asp Tyr Trp
225                 230                 235                 240
Gly Gln Gly Thr Leu Val Thr Val Ser Ser Gly Ser Ala Ser Ala Pro
                245                 250                 255
Thr Leu Phe Pro Ala Ala Ala His His His His His His Gly Ala Ala
            260                 265                 270
Glu Gln Lys Leu Ile Ser Glu Glu Asp Leu Asn Gly Ala Ala
        275                 280                 285
```

<210> SEQ ID NO 12
<211> LENGTH: 861
<212> TYPE: DNA
<213> ORGANISM: Artificial sequence
<220> FEATURE:
<223> OTHER INFORMATION: Synthetic construct

<400> SEQUENCE: 12

```
cagtctgtgt tgacgcagcc gccctcagtg tctgggtctc ctggacagtc gatcaccatc    60
tcctgcactg gaaccagcag tgatattggg acttataaaa ttgtctcctg gtaccaacag   120
cacccggca agccccccaa actcatgatt tatgacgtca atcagcggcc ctcaggggtt   180
tctgatcgct tctctggctc caagtctggc aacacggcct ccctgacaat ctctgggctc   240
caggctgagg acgaggctga ttattactgc agctcatata caagcggcag cactctggta   300
ttcggcgggg ggaccaagct gaccgtccta ggctcgagtg gtggaggcgg ttcaggcgga   360
ggtggctctg gcggtagtgc acttcaggta cagctgcagc agtcaggagc agaggtgaaa   420
aagcccgggg agtctctgaa gatctcctgt aagggttctg gatacagctt accagctac   480
tggatcggct gggtgcgcca gatgcccggg aaaggcctgg agtggatggg gatcatctat   540
cctggtgact ctgataccag atacagcccg tccttccaag gccaggtcac catctcagcc   600
gacaagtcca tcagcaccgc ctacctgcag tggagcagcc tgaaggcctc ggacaccgcc   660
atgtattact gtgcgagaca tcgggccgct agtgggagcc cggacgcgtg tgactactgg   720
ggccagggaa ccctggtcac cgtctcctca gggagtgcat ccgccccaac ccttttcccc   780
gcggccgcac atcatcatca ccatcacggg ccgcagaac aaaaactcat ctcagaagag   840
gatctgaatg gggccgcata g                                              861
```

<210> SEQ ID NO 13
<211> LENGTH: 15
<212> TYPE: PRT
<213> ORGANISM: Artificial sequence
<220> FEATURE:
<223> OTHER INFORMATION: Biotin lygase tag

<400> SEQUENCE: 13

```
Leu His His Ile Leu Asp Ala Gln Lys Met Val Trp Asn His Arg
1               5                  10                  15
```

<210> SEQ ID NO 14
<211> LENGTH: 238
<212> TYPE: PRT
<213> ORGANISM: Artificial sequence
<220> FEATURE:
<223> OTHER INFORMATION: Orange fluorescent protein

<400> SEQUENCE: 14

```
Met Ser Lys Gly Glu Glu Leu Phe Thr Gly Val Val Pro Ile Leu Val
1               5                   10                  15
Glu Leu Asp Gly Asp Val His Gly His Lys Phe Ser Val Arg Gly Glu
            20                  25                  30
Gly Glu Gly Asp Ala Asp Tyr Gly Lys Leu Glu Ile Lys Phe Ile Cys
        35                  40                  45
Thr Thr Gly Lys Leu Pro Val Pro Trp Pro Thr Leu Val Thr Thr Leu
    50                  55                  60
Gly Tyr Gly Ile Leu Cys Phe Ala Arg Tyr Pro Glu His Met Lys Met
65                  70                  75                  80
Asn Asp Phe Phe Lys Ser Ala Met Pro Glu Gly Tyr Ile Gln Glu Arg
                85                  90                  95
Thr Ile Phe Phe Gln Asp Asp Gly Lys Tyr Lys Thr Arg Gly Glu Val
            100                 105                 110
Lys Phe Glu Gly Asp Thr Leu Val Asn Arg Ile Glu Leu Lys Gly Met
        115                 120                 125
Asp Phe Lys Glu Asp Gly Asn Ile Leu Gly His Lys Leu Glu Tyr Asn
    130                 135                 140
Phe Asn Ser His Asn Val Tyr Ile Met Pro Asp Lys Ala Asn Asn Gly
145                 150                 155                 160
Leu Lys Val Asn Phe Lys Ile Arg His Asn Ile Glu Gly Gly Gly Val
                165                 170                 175
Gln Leu Ala Asp His Tyr Gln Thr Asn Val Pro Leu Gly Asp Gly Pro
            180                 185                 190
Val Leu Ile Pro Ile Asn His Tyr Leu Ser Tyr Gln Thr Ala Ile Ser
        195                 200                 205
Lys Asp Arg Asn Glu Thr Arg Asp His Met Val Phe Leu Glu Phe Phe
    210                 215                 220
Ser Ala Cys Gly His Thr His Gly Met Asp Glu Leu Tyr Lys
225                 230                 235
```

<210> SEQ ID NO 15
<211> LENGTH: 717
<212> TYPE: DNA
<213> ORGANISM: Artificial sequence
<220> FEATURE:
<223> OTHER INFORMATION: Orange fluorescent protein coding sequence

<400> SEQUENCE: 15

```
atgagtaaag gagaagaact tttcactgga gttgtcccaa ttcttgttga attagatggt    60
gatgtccatg gacataaaat tctctgtcaga ggagaagggg aaggcgatgc agattatgga   120
aaacttgaaa tcaaattcat ttgcactact ggaaagctac cagttccatg gccaacactt   180
gttactacac tgggctatgg catcctatgt ttcgcaagat acccagaaca catgaaaatg   240
aatgacttct tcaagagtgc catgcctgag ggttacattc aagaaagaac catcttttc    300
caagatgatg gaaaatacaa gacacgtggt gaagtcaagt ttgaaggtga tactcttgtt   360
aacagaattg agctcaaagg tatggacttt aagaagatg caatatcct tggacacaag     420
ttggagtaca atttaactc acataatgta tacattatgc cggacaaagc caataatgga   480
ctcaaagtca atttcaaaat tagacacaat atcgaaggtg gtggtgtcca actcgctgat   540
cattaccaaa caaatgttcc ccttggagac ggtcctgtcc ttataccaat caatcactac   600
```

```
ctatcctatc aaacagccat ttcaaaagat cgaaatgaga cgagagatca tatggtgttt      660
ctggaatttt tctcagcttg tggacataca catggcatgg atgaactata caaataa         717
```

<210> SEQ ID NO 16
<211> LENGTH: 1019
<212> TYPE: PRT
<213> ORGANISM: Artificial sequence
<220> FEATURE:
<223> OTHER INFORMATION: Beta-galactosidase

<400> SEQUENCE: 16

```
Met Ala Asp Pro Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg Pro Ser Gln Gln Leu Arg
        35                  40                  45

Ser Leu Asn Gly Glu Trp Arg Phe Ala Trp Phe Pro Ala Pro Glu Ala
    50                  55                  60

Val Pro Glu Ser Trp Leu Glu Cys Asp Leu Pro Glu Ala Asp Thr Val
65                  70                  75                  80

Val Val Pro Ser Asn Trp Gln Met His Gly Tyr Asp Ala Pro Ile Tyr
                85                  90                  95

Thr Asn Val Thr Tyr Pro Ile Thr Val Asn Pro Pro Phe Val Pro Thr
            100                 105                 110

Glu Asn Pro Thr Gly Cys Tyr Ser Leu Thr Phe Asn Val Asp Glu Ser
        115                 120                 125

Trp Leu Gln Glu Gly Gln Thr Arg Ile Ile Phe Asp Gly Val Asn Ser
    130                 135                 140

Ala Phe His Leu Trp Cys Asn Gly Arg Trp Val Gly Tyr Gly Gln Asp
145                 150                 155                 160

Ser Arg Leu Pro Ser Glu Phe Asp Leu Ser Ala Phe Leu Arg Ala Gly
                165                 170                 175

Glu Asn Arg Leu Ala Val Met Val Leu Arg Trp Ser Asp Gly Ser Tyr
            180                 185                 190

Leu Glu Asp Gln Asp Met Trp Arg Met Ser Gly Ile Phe Arg Asp Val
        195                 200                 205

Ser Leu Leu His Lys Pro Thr Thr Gln Ile Ser Asp Phe His Val Ala
    210                 215                 220

Thr Arg Phe Asn Asp Asp Phe Ser Arg Ala Val Leu Glu Ala Glu Val
225                 230                 235                 240

Gln Met Cys Gly Glu Leu Arg Asp Tyr Leu Arg Val Thr Val Ser Leu
                245                 250                 255

Trp Gln Gly Glu Thr Gln Val Ala Ser Gly Thr Ala Pro Phe Gly Gly
            260                 265                 270

Glu Ile Ile Asp Glu Arg Gly Gly Tyr Ala Asp Arg Val Thr Leu Arg
        275                 280                 285

Leu Asn Val Glu Asn Pro Lys Leu Trp Ser Ala Glu Ile Pro Asn Leu
    290                 295                 300

Tyr Arg Ala Val Val Glu Leu His Thr Ala Asp Gly Thr Leu Ile Glu
305                 310                 315                 320

Ala Glu Ala Cys Asp Val Gly Phe Arg Glu Val Arg Ile Glu Asn Gly
                325                 330                 335

Leu Leu Leu Leu Asn Gly Lys Pro Leu Leu Ile Arg Gly Val Asn Arg
            340                 345                 350
```

```
His Glu His His Pro Leu His Gly Gln Val Met Asp Glu Gln Thr Met
            355                 360                 365
Val Gln Asp Ile Leu Leu Met Lys Gln Asn Asn Phe Asn Ala Val Arg
    370                 375                 380
Cys Ser His Tyr Pro Asn His Pro Leu Trp Tyr Thr Leu Cys Asp Arg
385                 390                 395                 400
Tyr Gly Leu Tyr Val Val Asp Glu Ala Asn Ile Glu Thr His Gly Met
                405                 410                 415
Val Pro Met Asn Arg Leu Thr Asp Asp Pro Arg Trp Leu Pro Ala Met
            420                 425                 430
Ser Glu Arg Val Thr Arg Met Val Gln Arg Asp Arg Asn His Pro Ser
    435                 440                 445
Val Ile Ile Trp Ser Leu Gly Asn Glu Ser Gly His Gly Ala Asn His
    450                 455                 460
Asp Ala Leu Tyr Arg Trp Ile Lys Ser Val Asp Pro Ser Arg Pro Val
465                 470                 475                 480
Gln Tyr Glu Gly Gly Gly Ala Asp Thr Thr Ala Thr Asp Ile Ile Cys
                485                 490                 495
Pro Met Tyr Ala Arg Val Asp Glu Asp Gln Pro Phe Pro Ala Val Pro
            500                 505                 510
Lys Trp Ser Ile Lys Lys Trp Leu Ser Leu Pro Gly Glu Thr Arg Pro
    515                 520                 525
Leu Ile Leu Cys Glu Tyr Ala His Ala Met Gly Asn Ser Leu Gly Gly
    530                 535                 540
Phe Ala Lys Tyr Trp Gln Ala Phe Arg Gln Tyr Pro Arg Leu Gln Gly
545                 550                 555                 560
Gly Phe Val Trp Asp Trp Val Asp Gln Ser Leu Ile Lys Tyr Asp Glu
                565                 570                 575
Asn Gly Asn Pro Trp Ser Ala Tyr Gly Gly Asp Phe Gly Asp Thr Pro
            580                 585                 590
Asn Asp Arg Gln Phe Cys Met Asn Gly Leu Val Phe Ala Asp Arg Thr
    595                 600                 605
Pro His Pro Ala Leu Thr Glu Ala Lys His Gln Gln Gln Phe Phe Gln
    610                 615                 620
Phe Arg Leu Ser Gly Gln Thr Ile Glu Val Thr Ser Glu Tyr Leu Phe
625                 630                 635                 640
Arg His Ser Asp Asn Glu Leu Leu His Trp Met Val Ala Leu Asp Gly
                645                 650                 655
Lys Pro Leu Ala Ser Gly Glu Val Pro Leu Asp Val Ala Pro Gln Gly
            660                 665                 670
Lys Gln Leu Ile Glu Leu Pro Glu Leu Pro Gln Pro Glu Ser Ala Gly
    675                 680                 685
Gln Leu Trp Leu Thr Val Arg Val Val Gln Pro Asn Ala Thr Ala Trp
    690                 695                 700
Ser Glu Ala Gly His Ile Ser Ala Trp Gln Gln Trp Arg Leu Ala Glu
705                 710                 715                 720
Asn Leu Ser Val Thr Leu Pro Ala Ala Ser His Ala Ile Pro His Leu
                725                 730                 735
Thr Thr Ser Glu Met Asp Phe Cys Ile Glu Leu Gly Asn Lys Arg Trp
            740                 745                 750
Gln Phe Asn Arg Gln Ser Gly Phe Leu Ser Gln Met Trp Ile Gly Asp
    755                 760                 765
```

Lys Lys Gln Leu Leu Thr Pro Leu Arg Asp Gln Phe Thr Arg Ala Pro
770                 775                 780

Leu Asp Asn Asp Ile Gly Val Ser Glu Ala Thr Arg Ile Asp Pro Asn
785                 790                 795                 800

Ala Trp Val Glu Arg Trp Lys Ala Ala Gly His Tyr Gln Ala Glu Ala
            805                 810                 815

Ala Leu Leu Gln Cys Thr Ala Asp Thr Leu Ala Asp Ala Val Leu Ile
            820                 825                 830

Thr Thr Ala His Ala Trp Gln His Gln Gly Lys Thr Leu Phe Ile Ser
            835                 840                 845

Arg Lys Thr Tyr Arg Ile Asp Gly Ser Gly Gln Met Ala Ile Thr Val
850                 855                 860

Asp Val Glu Val Ala Ser Asp Thr Pro His Pro Ala Arg Ile Gly Leu
865                 870                 875                 880

Asn Cys Gln Leu Ala Gln Val Ala Glu Arg Val Asn Trp Leu Gly Leu
                885                 890                 895

Gly Pro Gln Glu Asn Tyr Pro Asp Arg Leu Thr Ala Ala Cys Phe Asp
                900                 905                 910

Arg Trp Asp Leu Pro Leu Ser Asp Met Tyr Thr Pro Tyr Val Phe Pro
            915                 920                 925

Ser Glu Asn Gly Leu Arg Cys Gly Thr Arg Glu Leu Asn Tyr Gly Pro
930                 935                 940

His Gln Trp Arg Gly Asp Phe Gln Phe Asn Ile Ser Arg Tyr Ser Gln
945                 950                 955                 960

Gln Gln Leu Met Glu Thr Ser His Arg His Leu Leu His Ala Glu Glu
                965                 970                 975

Gly Thr Trp Leu Asn Ile Asp Gly Phe His Met Gly Ile Gly Gly Asp
            980                 985                 990

Asp Ser Trp Ser Pro Ser Val Ser Ala Asp Phe Gln Leu Ser Ala Gly
            995                 1000                1005

Arg Tyr His Tyr Gln Leu Val Trp Cys Gln Lys
    1010                1015

<210> SEQ ID NO 17
<211> LENGTH: 3060
<212> TYPE: DNA
<213> ORGANISM: Artificial sequence
<220> FEATURE:
<223> OTHER INFORMATION: Beta-galactosidase coding sequene

<400> SEQUENCE: 17 ttattttga caccagacca actggtaatg gtagcgaccg gcgctcagct ggaaatccgc    60
cgatactgac gggctccagg agtcgtcgcc accaatcccc atatggaaac cgtcgatatt   120
cagccatgtg ccttcttccg cgtgcagcag atggcgatgg ctggtttcca tcagttgctg   180
ttgactgtag cggctgatgt tgaactggaa gtcgccgcgc cactggtgtg gccataatt    240 caattcgcgc gtcccgcagc gcagaccgtt ttcgctcggg aagacgtacg gggtatacat   300
gtctgacaat ggcagatccc agcggtcaaa acaggcggca gtaaggcggt cgggatagtt   360
ttcttgcggc cctaatccga ccagtttac ccgtctgct acctgcgcca gctggcagtt    420
caggccaatc cgcgccggat gcggtgtatc gctcgccact caacatcaa cggtaatcgc    480 catttgacca ctaccatcaa tccggtaggt tttccggctg ataaataagg ttttcccctg   540
atgctgccac gcgtgagcgg tcgtaatcag caccgcatca gcaagtgtat ctgccgtgca   600
ctgcaacaac gctgcttcgg cctggtaatg gcccgccgcc ttccagcgtt cgacccaggc   660

```
gttagggtca atgcgggtcg cttcacttac gccaatgtcg ttatccagcg gtgcacgggt    720
gaactgatcg cgcagcggcg tcagcagttg tttttatcg ccaatccaca tctgtgaaag     780
aaagcctgac tggcggttaa attgccaacg cttattaccc agctcgatgc aaaaatccat    840
ttcgctggtg gtcagatgcg ggatggcgtg ggacgcggcg gggagcgtca cactgaggtt    900
ttccgccaga cgccactgct gccaggcgct gatgtgcccg gcttctgacc atgcggtcgc    960
gttcggttgc actacgcgta ctgtgagcca gagttgcccg gcgctctccg gctgcggtag   1020
ttcaggcagt tcaatcaact gtttaccttg tggagcgaca tccagaggca cttcaccgct   1080
tgccagcggc ttaccatcca gcgccaccat ccagtgcagg agctcgttat cgctatgacg   1140
gaacaggtat tcgctggtca cttcgatggt ttgcccggat aaacggaact ggaaaaactg   1200
ctgctggtgt tttgcttccg tcagcgctgg atgcggcgtg cggtcggcaa agaccagacc   1260
gttcatacag aactggcgat cgttcggcgt atcgccaaaa tcaccgccgt aagccgacca   1320
cgggttgccg ttttcatcat atttaatcag cgactgatcc acccagtccc agacgaagcc   1380
gccctgtaaa cggggatact gacgaaacgc ctgccagtat ttagcgaaac cgccaagact   1440
gttacccatc gcgtgggcgt attcgcaaag gatcagcggg cgcgtctctc caggtagcga   1500
aagccatttt ttgatggacc atttcggcac agccgggaag ggctggtctt catccacgcg   1560
cgcgtacatc gggcaaataa tatcggtggc cgtggtgtcg gctccgccgc cttcatactg   1620
caccgggcgg gaaggatcga cagatttgat ccagcgatac agcgcgtcgt gattagcgcc   1680
gtggcctgat tcattcccca gcgaccagat gatcacactc gggtgattac gatcgcgctg   1740
caccattcgc gttacgcgtt cgctcatcgc cggtagccag cgcggatcat cggtcagacg   1800
attcattggc accatgccgt gggtttcaat attggcttca tccaccacat acaggccgta   1860
gcggtcgcac agcgtgtacc acagcggatg gttcggataa tgcgaacagc gcacggcgtt   1920
aaagttgttc tgcttcatca gcaggatatc ctgcaccatc gtctgctcat ccatgacctg   1980
accatgcaga ggatgatgct cgtgacggtt aacgcctcga atcagcaacg gcttgccgtt   2040
cagcagcagc agaccatttt caatccgcac ctcgcggaaa ccgacatcgc aggcttctgc   2100
ttcaatcagc gtgccgtcgg cggtgtgcag ttcaaccacc gcacgataga gattcgggat   2160
ttcggcgctc cacagtttcg ggttttcgac gttcagacgt agtgtgacgc gatcggcata   2220
accaccacgc tcatcgataa tttcaccgcc gaaaggcgcg gtgccgctgg cgacctgcgt   2280
ttcaccctgc cataaagaaa ctgttacccg taggtagtca cgcaactcgc cgcacatctg   2340
aacttcagcc tccagtacag cgcggctgaa atcatcatta aagcgagtgg caacatggaa   2400
atcgctgatt tgtgtagtcg gtttatgcag caacgagacg tcacggaaaa tgccgctcat   2460
ccgccacata tcctgatctt ccagataact gccgtcactc caacgcagca ccatcaccgc   2520
gaggcggttt tctccggcgc gtaaaaatgc gctcaggtca aattcagacg gcaaacgact   2580
gtcctggccg taaccgaccc agcgcccgtt gcaccacaga tgaaacgccg agttaacgcc   2640
atcaaaaata attcgcgtct ggccttcctg tagccagctt tcatcaacat taaatgtgag   2700
cgagtaacaa cccgtcggat tctccgtggg aacaaacggc ggattgaccg taatgggata   2760
ggttacgttg gtgtagatgg cgcatcgta accgtgcatc tgccagtttg aggggacgac   2820
gacagtatcg gcctcaggaa gatcgcactc cagccagctt tccggcaccg cttctggtgc   2880
cggaaaccag gcaaagcgcc attcgccatt caggctgcgc aactgttggg aagggcgatc   2940
ggtgcgggcc tcttcgctat tacgccagct ggcgaaaggg ggatgtgctg caaggcgatt   3000
aagttgggta acgccagggt tttcccagtc acgacgttgt aaaacgacgg gatcagccat   3060
```

```
<210> SEQ ID NO 18
<211> LENGTH: 159
<212> TYPE: PRT
<213> ORGANISM: Artificial sequence
<220> FEATURE:
<223> OTHER INFORMATION: streptavidin

<400> SEQUENCE: 18

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 19
<211> LENGTH: 483
<212> TYPE: DNA
<213> ORGANISM: Artificial sequence
<220> FEATURE:
<223> OTHER INFORMATION: streptavidin coding sequence

<400> SEQUENCE: 19
gacccgagca aagattctaa agcacaagta tctgctgcag aagcaggaat tacaggcaca      60
tggtataatc agctgggatc tacatttatt gttacagccg gcgcagatgg agctcttaca     120
ggaacatatg aatctgctgt tggaaatgca gaatctagat acgtgcttac aggaagatat     180
gattctgcac ctgcaacaga tggatccgga acagcacttg gatggacagt tgcatggaaa     240
aacaattata gaaacgcaca tagcgctaca acatggtctg gccaatatgt gggaggtgca     300
gaagcaagaa ttaacacaca atggctttta acatctggaa caacagaagc aaatgcatgg     360
aaaagtactc ttgttggaca tgatacattt acaaaagtta aacctagcgc agcatctatc     420
gatgcagcga aaaagcagg agttaacaat ggcaatcctt tagatgcagt tcaacaataa     480
tga                                                                    483
```

METHODS OF TREATING DIABETES AND COMPOSITIONS CAPABLE OF SAME

RELATED APPLICATIONS

This application is a National Phase of PCT Patent Application No. PCT/IL2011/000436 having International filing date of Jun. 2, 2011, which claims the benefit of priority under 35 USC §119(e) of U.S. Provisional Patent Application No. 61/350,943 filed on Jun. 3, 2010. The contents of the above applications are all incorporated by reference as if fully set forth herein in their entirety.

FIELD AND BACKGROUND OF THE INVENTION

The present invention, in some embodiments thereof, relates to compositions and methods for diagnosing and treating diabetes.

The transition of soluble peptides and proteins into highly-ordered amyloid structures is associated with major human disorders including Alzheimer's disease (AD), Parkinson's disease, Prion and Type II Diabetes (T2D). While amyloid fibrils were previously considered as the main pathological elements that facilitate the tissue degeneration observed in amyloid-related disorders, there is an increased body of evidence which suggest a key role for early soluble oligomeric assemblies in the process of cytotoxicity and cell death. A comprehensive postmortem study of AD-associated β-amyloid polypeptide (Aβ) aggregation showed poor correlation between amyloid plaque burden and cognitive functions in elderly population. This lead to the reexamination of the amyloid hypothesis regarding fibrils as the major toxic species in amyloid-associated diseases. Since this early work, a number of studies provided evidence that Aβ oligomers are in fact significantly more cytotoxic than mature fibrils. Moreover the intracranial reintroduction of purified soluble oligomer into the brain of normal rodents resulted in severe memory impairment. Revolutionary work has shown that it is possible to generate soluble toxic oligomeric forms of Aβ 1-42 in vitro [Lambert, M. P. et al. Proc. Natl. Acad. Sci. USA. 95, 6448-6453, (1998); Barghorn, S. et al. J. Neurochem. 95, 834-847, (2005). Braghorn et al. also demonstrated that although these assemblies were formed in vitro under relatively harsh conditions similar epitopes were also observed in vivo in AD patient's brains and in amyloid precursor protein transgenic mice [J. Neurochem. 95, 834-847, (2005)]. These epitopes are currently being used for the development of immunological treatment of AD.

In addition, several proteins that are not associated with any known disease can form oligomers-like structures in vitro [Caughey, B. & Lansbury, P. T. *Annu. Rev. Neurosci.* 26, 267-298, (2003)]. The observation that these newly formed structures exhibit toxicity similar to amyloid oligomers, suggest a much wider mechanism of toxicity not related to amyloid formation. Amyloid oligomers specifically increase lipid bilayer conductance regardless of the sequence, whereas fibrils and soluble low molecular weight species have no observable effect on membranes [Bucciantini, M. et al. *J. Biol. Chem.* 279, 31374-31382, (2004)].

The islet amyloid polypeptide (IAPP) is a 37 amino acid peptide hormone, packaged and secreted with insulin by pancreatic β-cells in secretory granules. Under normal conditions IAPP is released into the blood circulation and excreted via the renal system. IAPP is part of the endocrine system and contributes to glycemic control. This peptide is highly conserved between species, implying a functional significance. Type 2 Diabetes (T2D) is characterized by a disruption of insulin secretion from islet Langerhans cells and decreased insulin sensitivity of peripheral tissue. The first description of amyloid deposits in pancreatic islets of a diabetic subject was made more than 100 years ago. Islet amyloidosis can affect less than 1% or up to 80% of islets in a diabetic individual. The occurrence of islet amyloid in non-diabetic subjects is low, less than 15% in elderly, apparently non-diabetic individuals, but is high in more than 90% of diabetic subjects postmortem. In 1987, two groups identified the constitutive protein in islet amyloid, denoting it Amylin or IAPP. As other amyloid-related diseases, the amyloid deposits in pancreatic islets were considered as the primary toxic agent and as a primary cause of pancreatic degeneration for many years.

In the last decade this dogma was challenged by several studies suggesting that soluble oligomers may be the primary toxic species as islet amyloid is also found in non-diabetic individuals, particularly with elderly population, and is not present in all islets in people with T2D. Homozygous transgenic mice of human IAPP (hIAPP) developed severe diabetes due to a high rate of β-cell apoptosis already at the age of 10 weeks. However, extracellular islet amyloid was not yet present in these mice during the rapid loss of β-cells from age 5-10 weeks. In obese hemizygous hIAPP mice that develop diabetes at approximately 20 weeks of age, extensive islet amyloid does accrue, but there is a poor correlation between the extent of islet amyloid and the frequency of β-cell apoptosis.

Porat, Y., et al., *Biochemistry* 42, 10971-10977, (2003) showed that the soluble structures of the hIAPP peptide interact and destabilize biological membrane. By showing that inhibition of IAPP fibrillation by rifampicin did not inhibit toxicity towards pancreatic cells, Meier et al. [*Am. J. Physiol. Endocrinol. Metab.* 291, E1317-1324, (2006)] proved that oligomers are probably the primary toxic epitope in T2D.

In spite of the extensive clinical importance of amyloid oligomers formation in T2D, the molecular mechanism that leads to the self-assembly and molecular recognition process is still not fully understood and soluble oligomers were never stabilized as distinctive entities.

U.S. Patent Application Publication No. 20090246191 teaches crosslinked prefibrillar aggregates of IAPP and crosslinked forms of Beta amyloid oligomers.

Porat et al., [Biochem, 2003, 42, 10971-10977] teaches pre-fibrillar structures of IAPP having a beta sheet secondary structure.

SUMMARY OF THE INVENTION

According to an aspect of some embodiments of the present invention there is provided a composition of matter comprising isolated oligomers of human islet amyloid polypeptide (IAPP).

According to an aspect of some embodiments of the present invention there is provided a method of generating the composition of matter of the present invention, the method comprising:

(a) dissolving human IAPP in an agent that eliminates structured forms of IAPP;

(b) removing the agent;

(c) redissolving the non-structured form of IAPP in a solvent and an anionic surfactant, thereby generating the composition of matter of the present invention.

According to an aspect of some embodiments of the present invention there is provided a vaccine comprising oligomers of human IAPP and an immunologically acceptable carrier.

According to an aspect of some embodiments of the present invention there is provided a method of treating diabetes in a subject in need thereof, the method comprising administering to the subject an effective amount of the vaccine of the present invention, thereby treating diabetes in the subject.

According to an aspect of some embodiments of the present invention there is provided an isolated antibody which binds with a higher affinity to oligomers of human Islet Amyloid Polypeptide (IAPP) than fibrils of human IAPP.

According to an aspect of some embodiments of the present invention there is provided a pharmaceutical composition comprising as an active ingredient the isolated antibody of the present invention.

According to an aspect of some embodiments of the present invention there is provided a method of detecting IAPP oligomers in a biological sample, the method comprising contacting the biological sample with the antibody of the present invention under conditions which allow formation of immunocomplexes, wherein a presence of immunocomplexes above a predetermined threshold is indicative of IAPP oligomers in the biological sample.

According to an aspect of some embodiments of the present invention there is provided a method of diagnosing diabetes in a subject in need thereof, the method comprising detecting IAPP oligomers in a biological sample of the subject, wherein a presence or level above a predetermined threshold of the IAPP oligomers in the biological sample, is indicative of diabetes in the subject.

According to an aspect of some embodiments of the present invention there is provided a method of diagnosing diabetes in a subject in need thereof, the method comprising detecting antibodies which recognize IAPP oligomers in a biological sample of the subject, wherein a presence or level above a predetermined threshold of the antibodies in the biological sample, is indicative of diabetes in the subject.

According to an aspect of some embodiments of the present invention there is provided a method of treating diabetes in a subject in need thereof, the method comprising administering to the subject a therapeutic effective amount of an agent which reduces the activity or amount of an IAPP oligomer, thereby treating diabetes in the subject.

According to an aspect of some embodiments of the present invention there is provided a method of identifying an agent useful for treating diabetes, the method comprising contacting the agent with the composition of matter of claim 1, wherein a down-regulation of an amount or activity of the oligomers is indicative of an agent useful for the treatment of diabetes.

According to some embodiments of the invention, the oligomers comprise dimers and/or trimers.

According to some embodiments of the invention, the oligomers have a molecular weight between 4 kDa and 90 kDa.

According to some embodiments of the invention, the composition is devoid of fibrils of IAPP.

According to some embodiments of the invention, the composition of matter further comprising sodium dodecyl sulfate (SDS).

According to some embodiments of the invention, the oligomers have an alpha helical conformation.

According to some embodiments of the invention, the oligomers are crosslinked.

According to some embodiments of the invention, the oligomers are non-crosslinked.

According to some embodiments of the invention, the oligomers consist of dimers and/or trimers.

According to some embodiments of the invention, the composition of matter is stable for up to 7 days.

According to some embodiments of the invention, the agent is selected from the group consisting of 1,1,1,3,3,3 hexafluoro-2-propanol (HFIP), trifluoroethanol (TFE), and trifluoroacetic acid (TFA).

According to some embodiments of the invention, the solvent is selected from the group consisting of sodium hydroxide, potassium hydroxide, ammonium hydroxide, and dimethyl sulfoxide.

According to some embodiments of the invention, the anionic surfactant is selected from the group consisting of Sodium dodecyl sulfate (SDS), Ammonium lauryl sulfate, Docusate sodium salt, N-Lauroylsarcosine sodium salt, Lithium dodecyl sulfate, 1-Octanesulfonic acid sodium salt, Sodium 1-butanesulfonate, Sodium hexanesulfonate, Chenodeoxycholic acid, Dehydrocholic acid, Glycocholic acid and Sodium deoxycholate.

According to some embodiments of the invention, the isolated antibody is attached to an identifiable moiety.

According to some embodiments of the invention, the isolated antibody is a polyclonal antibody.

According to some embodiments of the invention, the isolated antibody is a monoclonal antibody.

According to some embodiments of the invention, the detecting is effected using the antibody of the present invention.

According to some embodiments of the invention, the agent is the antibody of the present invention.

According to some embodiments of the invention, the agent is a small molecule or an antibody.

According to some embodiments of the invention, the contacting is effected in the presence of cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 2A, 2B, 2C, 2D:
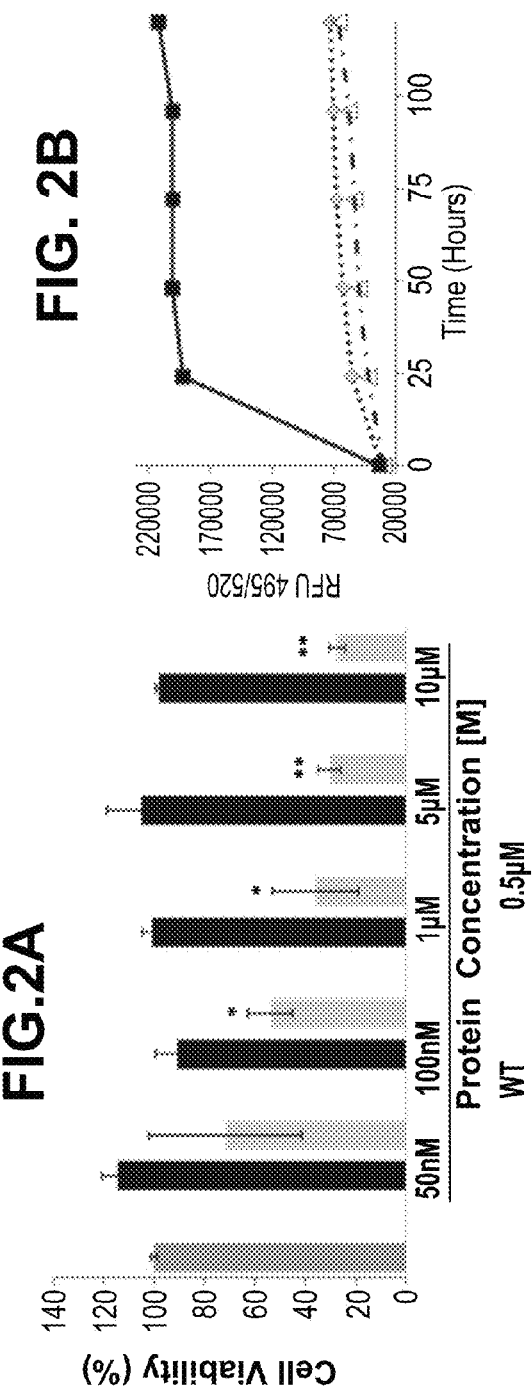

FIGS. 1A-E are graphs and photographs illustrating characterization of human IAPP oligomers. (FIG. 1A) PAGE analysis under non-reducing conditions of human IAPP oligomers and a negative control of non amyloidogenic rat IAPP (I-monomer, II-dimer and III-trimer). (FIG. 1B) Oligomer stability assay, hIAPP oligomers were dialyzed against PBS buffer and incubated at 37° C. Oligomer association/disassociation was monitored by PAGE analysis under non reducing conditions. (FIG. 1C) Size exclusion chromatography (Superdex 75 10/300, PBS buffer pH 7.4) of hIAPP oligomers; I-monomer, I-dimer, III-trimer and IV-90 kDa oligomer. (FIG. 1D) Transmittance electron microscopy (TEM) and atomic force microscopy (AFM) images of the ~90 kDa oligomers, TEM scale bar 100 nm, AFM scale bar 600 nm. (FIG. 1E) CD spectroscopy of hIAPP and rIAPP, protein concentration of 5 μM. Each spectrum represents the average of three measurements.

FIGS. 2A-D are graphs illustrating the toxicity of human IAPP oligomers. (FIG. 2A) Rin-m cells treated with hIAPP oligomers (grey) or with rIAPP (black) in diverse concentrations. Cell viability was estimated by MTT reduction assay (*$P<0.05$, **$P<0.005$). (FIG. 2B) Dye leakage from calcein containing liposomes. 1 μM hIAPP oligomers (black squares) or rIAPP (grey rhombus) were incubated with the liposomes, and membrane damage was evaluated by increased fluorescence (excitation: 495, emission: 520) and compared to the control group (white rectangle). (FIG. 2C) FACS results of the incubation of Rin-m cells with hIAPP oligomers at different concentrations. The Annexin V-FITC apoptosis detection kit was used for the detection of apoptotic cells. FL1-His the fluorescence of V-FITC and FL2-His the fluorescence of Annexin V-PE. I-cells in necrotic state, II-late apoptotic state, III-early apoptotic state and IV-viable cells (FIG. 2D) Diagram presentation of cell state dispersion of three FACS analysis assays, dark grey column represent viable cells, light grey column represent early and late apoptotic cells and black column represent necrotic cells.

FIG. 3 are confocal microscopic images illustrating that hIAPP oligomers permeabilize the cell membrane. Rin-m cells were incubated with 5 μM of hIAPP-Hiytelfluor 488 oligomers, and stained with phalloidin-tetramethylrhodamine. Incubation was performed for one hour (I), four hours (IV) and eight hours (VIII). After one hour, localization of hIAPP oligomers to the cell membrane was observed followed by insertion into the cytoplasm. Cell morphology alterations could be detected following longer incubation times.

FIGS. 4A-E are graphs and photographs illustrating that antibodies from Type II Diabetes patients recognize and neutralize hIAPP oligomers. (FIG. 4A) Purified antibodies from serum of type II diabetes patients and healthy people (N=3) was compared by analyzing their ability to recognize hIAPP oligomers (5 μg). Dot blot analysis was performed on serial dilutions of purified antibodies. (FIG. 4B) Densitometer analysis by Scion image of recognition properties of purified antibodies to hIAPP oligomers, light grey columns represent non type II diabetes antibodies and dark grey columns represents type II diabetes purified antibodies. (FIG. 4C) Rin-m cells treated with hIAPP oligomers (light grey, 5 μM) alone, Rin-m cells treated with hIAPP oligomers and Type II diabetes (orange) or non Type II diabetes (dark grey) purified antibodies in diverse concentration were examined for viability by MTT reduction assay and compared to the non-treated cells (black), (*$P<0.05$, **$P<0.005$). (FIG. 4D) PAGE analysis and Western-blot analysis of hIAPP oligomers was performed in order to study which of the multimers type II diabetes antibodies recognize. Positive control was performed with rabbit anti IAPP (Santa Cruz Biotechnology, USA) and negative control was done with non type II diabetes purified antibodies. (FIG. 4E) Bar graph illustrating the amount of antibody recognition in Type II diabetic patients as compared to non-Type II diabetic patients.

DESCRIPTION OF SPECIFIC EMBODIMENTS OF THE INVENTION

The present invention, in some embodiments thereof, relates to compositions and methods for diagnosing and treating diabetes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Soluble oligomeric assemblies of amyloid proteins emerge as the major pathological agent in degenerative misfolding diseases. Unlike the characterized Alzheimer's disease β-amyloid oligomers, the oligomeric state of the islet amyloid polypeptide (IAPP), was never stabilized, probed or manipulated. The present invention relates to the isolation of stable IAPP cytotoxic oligomers. These oligomers induce apoptosis in cultured pancreatic cells (FIGS. 2C-D), permeate model lipid vesicles (FIG. 3) and interact with the cell membrane following complete internalization (FIG. 3). Moreover, antibodies that specifically recognize these assemblies were exclusively identified in diabetes patients and were able to neutralize the apoptotic cytotoxic effect of these oligomers (FIGS. 4A-E). The present findings shows that human IAPP oligomers are not only stable and highly toxic to cultured cells, they are also found in Type II diabetes patients and accordingly play a major role in the disease progression.

The present inventors propose that vaccines comprising human IAPP oligomers may be useful for the treatment of Diabetes as well as antibodies capable of specifically recognizing the human IAPP oligomer.

Thus, according to one aspect of the present invention there is provided a composition of matter comprising isolated oligomers of human IAPP.

Islet amyloid polypeptide (IAPP) is a peptide hormone, consisting essentially of 37 amino acids, which is synthesized in the beta cells of the pancreas and which, together with insulin and glucagon, is involved in the regulation of sugar metabolism. IAPP is an antagonist of insulin.

The polynucleotide and polypeptide sequence of IAPP is set forth in Accession No. NM_000415 (SEQ ID NO: 1), NP_000406 (SEQ ID NO: 2), NM_010491 (SEQ ID NO: 3) AND NP_034621 (SEQ ID NO: 4).

As used herein, the term "oligomer" refers to covalent and non-covalent dimers and/or trimers or higher aggregates of IAPP that do not form fibrous structures i.e. regular β-sheet array (e.g. devoid of fibrils of IAPP).

The phrase "isolated oligomers" refers to the oligomers being substantially free from other substances (e.g., other pancreatic cells, blood components, hormones, proteins or nucleic acids, etc.) that are present in its in-vivo environment.

The isolated oligomers of the present invention are typically synthetically produced and are not part of an extract isolated from the pancreas or blood.

According to one embodiment, the isolated oligomers of the present invention comprise an α-helical secondary structure with globular morphology.

According to another embodiment, the molecular weight of the oligomers of the present invention is between about 4-90 kDa.

As used herein, the term "fibril" refers to a thread-like filamentous structure composed of higher ordered aggregates which is typically visible in an electron microscope.

Generation of the oligomers of this aspect of the present invention may be performed by:

(a) dissolving human IAPP in an agent that eliminates structured forms of IAPP;

(b) removing the agent; and (c) redissolving the non-structured form of IAPP in a solvent and an anionic surfactant.

The peptide human IAPP may be generated by solid phase peptide synthesis or by recombinant means. Large scale peptide synthesis is described by Andersson Biopolymers 2000; 55(3):227-50. Human IAPP is also commercially available—for example from Bachem, Bubendorf, Switzerland (H-7905).

Examples of agents which are capable of decreasing the amount of structure in human IAPP include, but are not limited to 1,1,1,3,3,3 hexafluoro-2-propanol (HFIP), trifluoroethanol (TFE), and trifluoroacetic acid (TFA).

Following dissolving of the IAPP, the dissolving agent is then removed (e.g. by drying, including air drying and drying under vacuum).

The non-structured form of IAPP is then redissolved in a solvent and an ionic surfactant.

Exemplary solvents that may be used according to this aspect of the present invention include sodium hydroxide, potassium hydroxide, ammonium hydroxide, and dimethyl sulfoxide.

Exemplary anionic surfactants that may be used according to this aspect of the present invention include Sodium dodecyl sulfate (SDS), Ammonium lauryl sulfate, Docusate sodium salt, N-Lauroylsarcosine sodium salt, Lithium dodecyl sulfate, 1-Octanesulfonic acid sodium salt, Sodium 1-butanesulfonate, Sodium hexanesulfonate, Chenodeoxycholic acid, Dehydrocholic acid, Glycocholic acid and Sodium deoxycholate.

According to a specific embodiment, the agent used to dissolve IAPP is 1,1,1,3,3,3 hexafluoro-2-propanol (HFIP), the solvent used to redissolve the non-structured form of IAPP is NaOH and the anionic surfactant used is SDS.

The present inventors showed that IAPP oligomers generated according to the above described protocol are stable for up to 7 days. In order to enhance stability, the oligomers may be crosslinked. Methods of crosslinking IAPP oligomers are disclosed in U.S. Patent Application Publication No. 20090246191, the contents of which are incorporated herein by reference. It will be appreciated that in the absence of crosslinking, the IAPP oligomers typically are no greater than trimers, such that compositions comprising the non-crosslinked oligomers of this aspect of the present invention are devoid of pentamers and/or hexamers.

The IAPP oligomers of this aspect of the present invention may be used for a variety of applications e.g. to isolate and/or purify oligomer reactive antibodies or fragments thereof from biological fluids. In another embodiment, the purified IAPP oligomers may be used to screen for and detect IAPP-oligomer reactive antibodies or fragments thereof in a biological sample. The purified oligomers may be used as a ligand in these methods. The oligomers may also be used as an immunogen to induce production of antibodies which specifically recognize the oligomeric state of IAPP.

Thus, according to another aspect of the present invention there is provided an isolated antibody which is capable of specifically binding to IAPP oligomers. Such antibodies bind with a higher affinity to oligomers of human Islet Amyloid Polypeptide (IAPP) than fibrils of human IAPP.

According to one embodiment of this aspect of the present invention, the antibodies bind with at least a two fold, preferably at least a 5 fold, even more preferably at least a 10 fold and even more preferably at least a 20 fold higher affinity for the oligomeric over the fibrillar form of IAPP.

According to another embodiment of this aspect of the present invention, the antibodies bind with the same affinity to the oligomeric IAPP and to the fibrillar form of IAPP.

According to still another embodiment of this aspect of the present invention, the antibodies bind with at least a two fold higher affinity to IAPP oligomers, more preferably at least a 5 fold higher affinity, more preferably at least a 10 fold higher affinity, more preferably at least a 20 fold higher affinity than to other amyloidogenic oligomers (e.g. serum amyloid A protein, beta2-microglobulin, transthyretin, cystatin C variant, gelsolin, procalcitonin, PrP protein, amyloid beta-protein, ApoA1, and lysozyme).

As used herein, the term "antibody" refers to a substantially intact antibody molecule or an antibody fragment.

The phrase "isolated antibody" refers to an antibody which has been removed from its natural environment. For example, the present inventors have isolated anti-IAPP oligomer antibodies onto a filter using a dot-blot assay (see FIG. 4A).

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker;

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

Methods for producing and screening for specific antibodies using hybridoma technology are routine and well known in the art. In a non-limiting example, mice can be immunized with the isolated oligomers of the present invention. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding the fibrils of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with the fibrils of the invention with myeloma cells and then screening the hybridomas resulting from the fusion for hybridoma clones that secrete an antibody able to bind the fibrils.

Antibodies also can be generated in vitro, e.g., using recombinant antibody binding site expressing phage display libraries, in addition to the traditional in vivo methods using animals. See, e.g., Huse Science 246:1275 (1989); Ward Nature 341:544 (1989); Hoogenboom Trends Biotechnol. 15:62-70 (1997); Katz Annu. Rev. Biophys. Biomol. Struct. 26:27-45 (1997).

In cases where target antigens are too small to elicit an adequate immunogenic response when generating antibodies in vivo, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in *E. coli* or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as *E. coli*. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of Escherichia coli. Biotechnology (N.Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

It will be appreciated that for human therapy or diagnostics, humanized antibodies are preferably used. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunisation. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633,425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

The antibodies of this aspect of the present invention may be attached to a functional moiety, such as a detectable moiety. Such antibodies may be useful for identifying IAPP oligomers.

Various types of detectable or reporter moieties may be conjugated to the antibody of the invention. These include, but not are limited to, a radioactive isotope (such as [125] iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimer or tetramer form of the antibody).

Table 1 provides non-limiting examples of identifiable moieties which can be conjugated to the antibody of the invention.

TABLE 1

| Identifiable Moiety | Amino Acid sequence (GenBank Accession No.) | Nucleic Acid sequence (GenBank Accession No.) |
|---|---|---|
| Green Fluorescent protein | AAL33912 (SEQ ID NO: 5) | AF435427 (SEQ ID NO: 6) |
| Alkaline phosphatase | AAK73766 (SEQ ID NO: 7) | AY042185 (SEQ ID NO: 8) |
| Peroxidase | CAA00083 (SEQ ID NO: 9) | A00740 (SEQ ID NO: 10) |
| Histidine tag | Amino acids 264-269 of GenBank Accession No. AAK09208 (SEQ ID NO: 11) | Nucleotides 790-807 of GenBank Accession No. AF329457 (SEQ ID NO: 12) |
| Myc tag | Amino acids 273-283 of GenBank Accession No. AAK09208 (SEQ ID NO: 11) | Nucleotides 817-849 of GenBank Accession No. AF329457 (SEQ ID NO: 12) |
| Biotin lygase tag | LHHILDAQKMVWNHR/ (SEQ ID NO: 13) | |
| orange fluorescent protein | AAL33917 (SEQ ID NO: 14) | AF435432 (SEQ ID NO: 15) |
| Beta galactosidase | ACH42114 (SEQ ID NO: 16) | EU626139 (SEQ ID NO: 17) |
| Streptavidin | AAM49066 (SEQ ID NO: 18) | AF283893 (SEQ ID NO: 19) | immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol. Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996.

As mentioned, the antibodies of the present invention may be used for detection of oligomeric IAPP in a biological sample.

Thus, according to another aspect of the present invention there is provided a method of detecting IAPP oligomers in a biological sample, the method comprising contacting the biological sample with the antibody of the present invention under conditions which allow formation of immunocomplexes, wherein a presence of immunocomplexes above a predetermined threshold is indicative of IAPP oligomers in the biological sample.

Biological sample may include tissues (e.g. pancreatic islets), cells, extracellular matrix, and biological fluids. Biological fluids include but are not limited to blood, plasma, serum, cerebrospinal fluid, urine, peritoneal fluid, and saliva.

According to this aspect the contacting may be effected in vitro, ex vivo or in vivo.

The immunocomplex of the present invention can be formed at a variety of temperatures, salt concentration and pH values and those of skills in the art are capable of adjusting the conditions suitable for the formation of each immunocomplex.

Determining a presence or level of the immunocomplex of the invention is dependent on the detectable moiety to which the antibody is attached, essentially as described hereinabove.

Since the present inventors have shown that oligomeric IAPP is associated with Diabetes, it follows that the antibodies may therefore be used for the diagnosis of Diabetes.

Thus, according to another aspect of the present invention there is provided a method of diagnosing Diabetes in a subject in need thereof, the method comprising detecting IAPP oligomers in a biological sample of the subject, wherein a presence or level above a predetermined threshold of the IAPP oligomers in the biological sample is indicative of Diabetes in the subject.

As mentioned herein above, the present inventors have shown that Diabetic patients generate antibodies which recognize oligomeric IAPP, whereas such antibodies are absent in non-diabetic patients. The present inventors thus propose that such antibodies may be used as a marker for Diabetes.

Thus, according to still another aspect of the present invention there is provided a method of diagnosing diabetes in a subject in need thereof, the method comprising detecting antibodies which recognize IAPP oligomers in a biological sample of the subject, wherein a presence or level above a predetermined threshold of the antibodies in the biological sample, is indicative of diabetes in the subject.

As used herein the term "diagnosing" refers to confirming the presence of Diabetes, classifying Diabetes, determining a severity of Diabetes (grade or stage), monitoring Diabetes progression, forecasting an outcome of Diabetes and/or prospects of recovery.

The subject may be a healthy subject (e.g., human) undergoing a routine well-being check up. Alternatively, the subject may be at risk of having Diabetes (e.g., a genetically predisposed subject, a subject with medical and/or family history of Diabetes) and/or a subject who exhibits suspicious clinical signs of Diabetes [e.g., a presence of sugar in the urine).

According to one embodiment, the level of immunocomplex (IAPP oligomer-antibody) is compared to a control sample from a non-diseased subject, wherein an up-regulation of immunocomplex formation is indicative of Diabetes. Preferably, the subject is of the same species e.g. human, preferably matched with the same age, weight, sex etc. It will be appreciated that the control sample may also be of the same subject from a healthy tissue, prior to disease progression or following disease remission.

The contacting may be ex vivo (from a sample removed from the subject) or in vivo.

Since the present inventors have now ascertained that it is the oligomeric form of IAPP that is toxic to islets, the present inventors propose that an agent which is capable of reducing the activity or amount of IAPP may be used for the treatment of Diabetes.

Thus, according to yet another aspect of the present invention there is provided a method of treating Diabetes in a subject in need thereof, the method comprising administering to the subject a therapeutic effective amount of an agent which reduces the activity or amount of an IAPP oligomer, thereby treating diabetes in the subject.

As used herein "Diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

According to a particular embodiment, the method is for treating type II Diabetes.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

According to one embodiment, the agents reduce the amount or activity of IAPP oligomers by at least 1.25 fold, more preferably by at least 1.5 fold, more preferably by at least 2 fold and even more preferably by at least 5 fold.

Agents which reduce the amount or activity of IAPP oligomers include but are not limited to antibodies directed against the oligomers, polynucleotide agents, peptide agents and small molecule agents.

Selection of agents which down-regulate the amount of IAPP oligomers may be performed by contacting the candidate agent and the isolated IAPP oligomers of the present invention, wherein a down-regulation of an amount of the oligomers is indicative of an agent useful for the treatment of diabetes.

The amount of IAPP oligomers may be estimated using any protein quantification method which are known in the art. Visualization of the oligomers may be effected by Page analysis, by size exclusion chromatography, circular dichroism spectroscopy, transmission electronic microscopy and atomic force microscopy.

In addition, the amount of IAPP oligomers may be estimated by analyzing their activity, as described herein below.

Selection of agents which down-regulate the activity of IAPP oligomers may be performed by contacting the candidate agent and the isolated IAPP oligomers of the present invention with cells (or artificial cells as described herein below), wherein a down-regulation of an activity of the oligomers is indicative of an agent useful for the treatment of diabetes.

The phrase "reduction of activity of IAPP oligomers" refers to reduction of the cytotoxic activity of the oligomers.

Contacting cells with the candidate agent and oligomers can be performed by any in vitro conditions including for example, adding the candidate agent and oligomers to cells derived from a subject (e.g., a primary cell culture, a cell line) or to a biological sample comprising same (e.g., a fluid, liquid which comprises the cells) such that both the candidate agent and the oligomers are in direct contact with the cells. According to some embodiments of the invention, the cells of the subject are incubated with the agent and oligomers. The conditions used for incubating the cells are selected for a time period/concentration of cells/concentration of drug/ratio between cells and candidate agent/oligomers and the like which enable the candidate agent to induce changes to the oligomers.

Methods of monitoring cellular changes induced by the drugs are known in the art and include for example, the MTT test which is based on the selective ability of living cells to reduce the yellow salt MTT (3-(4, 5-dimethylthiazolyl-2)-2, 5-diphenyltetrazolium bromide) (Sigma, Aldrich St Louis, Mo., USA) to a purple-blue insoluble formazan precipitate; the BrDu assay [Cell Proliferation ELISA BrdU colorimetric kit (Roche, Mannheim, Germany]; the TUNEL assay [Roche, Mannheim, Germany]; the Annexin V assay [ApoAlert® Annexin V Apoptosis Kit (Clontech Laboratories, Inc., CA, USA)]; the Senescence associated-β-galactosidase assay (Dimri G P, Lee X, et al. 1995. A biomarker that identifies senescent human cells in culture and in aging skin in vivo. Proc Natl Acad Sci USA 92:9363-9367); as well as various RNA and protein detection methods (which detect level of expression and/or activity) which are further described hereinabove.

As described in the Examples section herein below, the cytotoxic activity of the IAPP oligomers may also be analyzed using synthetic membranes—e.g. liposomes, since the ability to penetrate a cell membrane is thought to be directly correlated with IAPP cytotoxic activity.

Agents which are capable of down-regulating the amount or activity of the IAPP oligomers may be provided to the subject per se, or as part of a pharmaceutical composition where it is mixed with a pharmaceutically acceptable carrier.

As used herein a 'pharmaceutical composition' refers to a preparation of one or more of the active ingredients described herein with other chemical components such as physiologically suitable carriers and excipients. The purpose of a pharmaceutical composition is to facilitate administration of a compound to the subject treated.

Herein the term 'active ingredient' refers to the compound, which is accountable for the biological effect.

Hereinafter, the phrases 'physiologically acceptable carrier' and 'pharmaceutically acceptable carrier' which may be interchangeably used refer to a carrier or a diluent that does not cause significant irritation to the subject and does not abrogate the biological activity and properties of the administered compound. Preferred carriers of the pharmaceutical composition of the present invention include, but are not limited to, polyethylene glycol (PEG), a biocompatible polymer with a wide range of solubility in both organic and aqueous media (Mutter et al. (1979).

Herein the term 'excipient' refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in 'Remington's Pharmaceutical Sciences,' Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into a specific region of a patient's body (e.g. pancreas or liver).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

According to another aspect of the present invention, there is provided an article-of-manufacture including a packaging material and a pharmaceutical composition identified for treating amyloid associated diseases (e.g. Diabetes) being contained within the packaging material, the pharmaceutical composition including, as an active ingredient, the compound described hereinabove, and a pharmaceutically acceptable carrier.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the use of other agents (e.g., insulin) and diets (low sugar) can be used in combination with the agents of the present invention to increase therapeutic efficacy thereof.

Since the present inventors found antibodies to the IAPP oligomers in the serum of Diabetic patients, the present inventors conceive that the IAPP oligomers may be used as a vaccine for the treatment of Diabetes, so as to induce generation of antibodies in vivo.

Thus, according to another aspect of the present invention there is provided a vaccine comprising oligomers of human IAPP and an immunologically acceptable carrier.

General methods to prepare immunogenic or vaccine compositions are described in Remington's Pharmaceutical Science; Mack Publishing Company Easton, Pa. (latest edition). To increase immunogenicity, the polypeptides of the present invention may be adsorbed to or conjugated to beads such as latex or gold beads, ISCOMs, and the like. Immunogenic compositions may comprise adjuvants, which are substance that can be added to an immunogen or to a vaccine formulation to enhance the immune-stimulating properties of the immunogenic moiety. Liposomes are also considered to be adjuvants (Gregoriades, G. et al., Immunological Adjuvants and Vaccines, Plenum Press, New York, 1989) Examples of adjuvants or agents that may add to the effectiveness of proteinaceous immunogens include aluminum hydroxide, aluminum phosphate, aluminum potassium sulfate (alum), beryllium sulfate, silica, kaolin, carbon, water-in-oil emulsions, and oil-in-water emulsions. One type of adjuvant is muramyl dipeptide (MDP) and various MDP derivatives and formulations, e.g., N-acetyl-D-glucosaminyl-(.beta.1-4)-N-acetylmuramyl-L-alanyl-D-isoglutami-ne (GMDP) (Hornung, R L et al. Ther Immunol 1995 2:7-14) or ISAF-1 (5% squalene, 2.5% pluronic L121, 0.2% Tween 80 in phosphate-buffered solution with 0.4 mg of threonyl-muramyl dipeptide; see Kwak, L W et al. (1992) N. Engl. J. Med., 327:1209-1238). Other useful adjuvants are, or are based on, cholera toxin, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives such as QS21 (White, A. C. et al. (1991) Adv. Exp. Med. Biol., 303:207-210) which is now in use in the clinic (Helling, F et al. (1995) Cancer Res., 55:2783-2788; Davis, T A et al. (1997) Blood, 90: 509), levamisole, DEAE-dextran, blocked copolymers or other synthetic adjuvants. A number of adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen (oil-in-water), Alhydrogel (aluminum hydroxide), or a mixture of Amphigen and Alhydrogel. Aluminum is approved for human use.

The present invention also contemplates therapeutic compositions and methods comprising antibodies or an antiserum induced in one subject using the peptides of the present invention, removed from that subject and used to treat another subject by passive immunization or transfer of the antibodies.

The amount of IAPP oligomer to be administered depends on the health and weight of the recipient, the route of administration, the existence of other concurrent treatment, if any, the frequency of treatment, the nature of the effect desired, and the judgment of the skilled practitioner.

An exemplary dose for treating a subject is an amount of up to about 100 milligrams of oligomer per kilogram of body weight. A typical single dosage of the oligomer is between about 1 ng and about 100 mg/kg body weight, and preferably from about 10 µg to about 50 mg/kg body weight. A total daily dosage in the range of about 0.1 milligrams to about 7 grams is preferred for intravenous administration. A useful dose of an antibody for passive immunization is between 10-100 mg/kg. It has been suggested that an effective in vivo dose of an antibody/antiserum is between about 10- and 100-fold more than an effective neutralizing concentration or dose in vitro. These dosages can be determined empirically in conjunction with the present disclosure and state-of-the-art. The oligomers of the present invention may be administered alone or in conjunction with other therapeutics directed to the treatment of the disease or condition.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Oligomer Preparation:

IAPP synthetic peptide (Human; H-7905, Bachem, Bubendorf, Switzerland. Rat; 74-5-10A, American peptide, California, U.S.A) was suspended in 100% 1,1,1,3,3,3 hexafluoro-2-propanol (HFIP) at 1 mg/ml and incubated for complete solubilization under shaking (100 rpm) at 37° C. for 2 hours. HFIP was removed by Speedvac apparatus and peptide was resuspended in 0.2 µM NaOH to a final concentration of 5 mM, sonicated for 2 minutes in a pre-chilled sonication bath to ensure complete solubilization. Peptide was diluted in phosphate-buffered saline (PBS) with 1% Sodium Dodecyl Sulfate (SDS) to a final concentration of 600 µM and incubated for 4-7 hours, at 37° C. Peptide was further diluted in ultra pure $H_2O$ to a final concentration of 200 µM and incubated for 12 hours, 37° C. IAPP self-assembly products were analyzed by 15% Tris-tricine PAGE and stained with Imperial protein stain. For cell and liposome experiments, oligomers were precipitated by a nine fold excess (v/v) of ice-cold methanol/acetic acid solution (33% methanol, 4% acetic acid) for 1 hour at 4° C. The oligomers was then pelleted (10 min at 16,200 g), resuspended in PBS buffer, pH 7.4. In order to make sure SDS is removed entirely, samples were dialyzed against PBS buffer over night. IAPP oligomers were examined after treatment by PAGE analysis and size exclusion chromatography. They showed no change in size distribution.

Size Exclusion Chromatography:

IAPP oligomers (0.1 mg) were loaded on Superdex 75 column 10/300 (Amersham Biosciences, Sweden), 0.5 ml/min, phosphate-buffer saline (PBS). Size was determined using a calibration curve calculated with 5 protein standard (Bio-Rad. USA). Peaks Deconvolution was calculated by PeakFit software (SYSTAT software Inc.).

Transmission Electronic Microscopy:

TEM experiments were performed using a JEOL JEM1200EX microscope operating at 120 kV. Oligomer solution (8 µl) was placed on a 300 mesh formvar-coated grid and after 2 minutes, the excess fluid was removed with a filter paper. The samples were negatively stained with 8 µl uranyl acetate 1% for 2 min.

Atomic Force Microscopy:

AFM analysis was generated by depositing an aliquot of 40 µl on a freshly cleaved mica surface. Samples were probed by a Digital Instrument (DI) MultiMode™ Nano-Scope IV AFM, using a Mikromasch NSC15/Si3N4 cantilever (resonant frequency f=325 kHz, spring constant k=40 N/m) in a tapping mode.

Circular Dichroism (CD) Spectroscopy:

CD spectra were obtained using an AVIV 202 spectropolarimeter equipped with a temperature-controlled sample holder and a 10 mm path length cuvette.

All experiments were performed in PBS, pH 7.4, peptides concentration of 5 µM. For wavelength scan experiments, each spectrum represents the average of three scans. Evaluation of the secondary structure composition obtained from far-UV CD spectra was facilitated by using the K2d and CDNN software.

Liposome Membrane Damage Measurements:

Phosphatidyl ethanolamine, Phosphatidyl serine and phosphatidyl choline (Avanti, USA) in a molar ratio of 5:3:2 respectively, were dissolved in chloroform at a concentration of 20 mg/ml. Solvent was removed from the sample by evaporating the chloroform under a stream of nitrogen gas in a rotor vapor apparatus to deposit a thin lipid film on the walls of a glass test tube. The dry lipid film was then rehydrated in the 50 mM sodium phosphate buffer (pH 7.4) containing 40 mM sodium calcein to make multilamellar vesicles (MLVs) at a concentration of 40 mg/ml. The MLVs were then subjected to several sonication cycles to equilibrate the vesicles with the buffer. Nonencapsulated calcein was removed from vesicles through size exclusion chromatography using a HiPrep 16/60 sephacryl S-100 column (Amersham Pharmacia Biotech, Uppsala, Sweden). packed vesicles with calcein were confirmed by fluorescent measurements before and after adding 1% of triton x-100. Samples were incubated at 37° C. and the membrane damage rate was followed by Fluorescence assay (excitation at 495 nm, 2.5 nm slit, and emission at 520 nm, 5 nm slit). Measurements were taken using a Jobin Yvon Horiba Fluoromax-3 fluorimeter. Each point represents the average of three independent measurements.

MTT Reduction Assay:

Rin-m cells ($2\times10^5$ cells/ml) were cultured in 96-well micro plates (100 µl/well) and incubated overnight at 37° C. Human oligomers and rat IAPP was added to each well at various concentrations. Each measurement was repeated four times. Following incubation for 6 hours at 37° C., cell viability was evaluated using 3-(4,5-dimethylthiazolyl-2)-2, 5-diphenyltetrazolium bromide (MTT) assay. Briefly, 20 µL of 5 mg/ml MTT dissolved in PBS was added to each well. After 4 hours incubation at 37° C., 100 µl of extraction buffer [20% SDS dissolved in a solution of 50% dimethyl-formamide and 50% DDW (pH 4.7)] was added to each well, and the plates were incubated again overnight at 37° C. Finally, color intensity was measured using an ELISA plate reader at 570 nm.

Flow Cytometry Cell Sorting (FACS) Assay:

Rin-m cells ($5\times10^5$ cells/ml) were cultured for 4 hours at 37° C. incubated with human IAPP oligomers (final concentration of 0.5 µM, 1 µM and 5 µM). Samples were washed with PBS buffer and resuspended with 500 µl binding buffer. 5 µl of Annexin V-FITC and 10 µl of propidium iodide (Annexin V-FITC apoptosis detection kit; MBL) was added to the samples. After 10 minutes of incubation in the dark at RT, samples were analyzed using the FACS Sort (Beckton Dickinson) and results analyzed using the CellQuest program (Beckton Dickinson). Each measurement was repeated three times. FL1-H represents the fluorescence of V-FITC and FL2-H represents the fluorescence of annexin V-PE.

Confocal Microscopy:

Rin-m cells were cultured on glass cover slips located in 24-well micro plates, then incubated for different periods with hIAPP-Hiytelfluor 488 (Anaspec, USA) oligomers (5 µM) at 37° C., as described in the cell cytotoxicity experiments section. After incubation cells were washed with PBS buffer and fixed with 4% paraformaldehyde in PBS for 5 minutes and washed with PBS buffer. Cells were treated with 1% Triton x-100 in PBS and stained with 50 µg/ml Phalloidin Tetramethyl-rhodamine B isothiocyanate (Sigma-Aldrich) in PBS 40 minutes in room temperature, followed by extensive wash with PBS buffer. The cells were imaged using LSM 510 confocal laser scanning microscope (Carl Zeiss Jena, Germany).

Antibody Purification:

Antibodies from three healthy and three type II diabetes patients serum (Bioreclamation, USA) were purified by protein A column (GE healthcare). 1 ml of Human Serum was diluted 1:20 with loading buffer (20 mM $Na_2HPO_4$, 2 mM $NaH_2PO_4$ pH=7) and loaded onto a 5-ml protein A column flow throw was collected and reloaded 3 times. Bound antibody was eluted with 0.1 M of citric acid (pH 3.0) and neutralized with 1 M Tris-HCl (pH 9.0) for 1 ml of eluate 200 µl of Tris buffer was added. Protein-containing fractions were combined, dialyzed against 2 liter PBS buffer (16 h, 4° C.), antibodies concentration was determined using Bradford reagent (Sigma-Aldrich).

Antibody Recognition Assay:

In order to examine antibody recognition, hIAPP oligomers (5 µg) were applied via a vacuum manifold onto a nitrocellulose membrane. After blocking the membrane with 5% milk in TBS-T (50 mM tris, 150 mM NaCl pH=7.5 with 0.3% tween 80) for 1 hour at room temperature, the membrane was washed briefly with TBS and incubated with purified antibodies at several concentrations for 2 hours, room temperature. Then, the membrane was washed briefly with TBS-T and incubated with HRP-conjugated donkey anti human HRP antibody (Jackson immunoResearch laboratories, USA). The membrane was developed using ECL reagents (NEN, USA) according to the supplier's instructions or 3,3',5,5'-tetramethylbenzidine (TMB). Positive control was done with rabbit anti IAPP antibody (Santa Cruz Biotechnology, USA). Bound antibodies were quantified by Scion image densitometry software (Scion Corporation, USA). In order to examine which of the assemblies' type II diabetes antibodies recognize, hIAPP oligomers were separated by 15% Tris-tricine PAGE and blotted on a nitrocellulose membrane by Trans-Blot semi-dry transfer cell (Bio-Rad, USA). Binding assay was done the same as the dot-blot assay with 5 µg/ml antibodies concentration.

Antibody Neutralizing Effect:

Rin-m cells ($2 \times 10^5$ cells/ml) were cultured in 96-well micro plates (100 µl/well) and incubated overnight at 37° C. Human oligomers (5 µM) with or without antibodies was added to each well at various concentrations. Each measurement was repeated four times; also, a control measurement with antibodies alone at the highest concentration was preformed to refute any effect of antibodies on cell viability. Following incubation for 6 hours at 37° C., cell viability was evaluated using 3-(4,5-dimethylthiazolyl-2)-2,5-diphenyltetrazolium bromide (MTT) assay as described above.

RESULTS

Lyophilized hIAPP was dissolved in 1,1,1,3,3,3 hexafluoro-2-propanol (HFIP) to eliminate any pre-existing structures, after evaporation it was resuspended in 0.2 mM NaOH and further diluted in phosphate buffer with 1% sodium dodecyl sulfate (SDS). SDS is commonly-used as a chaotrophic agent; however, it can be used to stabilize amyloid oligomers by producing a membrane like environment.

In order to ascertain the exact nature of the assemblies formed, the present inventors analyzed the resulting protein species using several complementary methods. First, using PAGE analysis under non-reducing conditions, the present inventors observed three major assembly species: monomers of ~3.9 kDa, dimers of ~8 kDa and trimers of ~12 kDa (FIG. 1A). As a negative control, rat IAPP peptide (rIAPP) was analyzed, which differs by three residues and do not self assembles to form amyloid structures[30]. Indeed, as expected, only the monomeric conformation with rIAPP was observed (FIG. 1A). The oligomeric structures, once assembled, were stable for up to seven days without obvious disassembly or further polymerization to fibrils (FIG. 1B).

In addition, the size distribution was analyzed under more "native" conditions using fast liquid chromatography (FPLC) performed under physiological conditions (PBS pH 7.4) (FIG. 1C). Samples were loaded on a Superdex 75 HR10/300 column and their molecular weight was determined using calibration curve. Using this assay, the three species previously observed in the gel analysis were observed together with an additional species of ~90 kDa. This conformer is probably not stable in SDS-PAGE and disassembles to smaller multimers. Size exclusion chromatography did not show evidence for larger assemblies which insinuates that amyloid fibrils were not formed.

The morphology of the oligomers was examined by transmission electron microscopy (TEM) and atomic force microscopy (AFM), (FIG. 1D). Using these methods only the ~90 kDa oligomer could be detected. These experiments revealed that no fibrillar aggregates are present and the oligomers posses a spherical morphology with a diameter of 5-30 nm as seen in TEM and a similar height (Z-axis) dimension, which ranged between 8-35 nm, as measured by AFM. Secondary structure determination was performed by circular dichroism analysis (CD) in the far UV (200-240 nm) (FIG. 1E). CD spectra indicated a predominant α-helical structure with two negative peaks at 222 and 208 nm. The rIAPP treated in the same manner exhibit lower α-helical content and higher β-sheet and random coil structures. Importantly, the CD spectrum in analysis showed no evidence of β-sheet structure indicative of amyloid fiber formation. Several studies have shown hIAPP adopts α-helical structure upon its interaction with biological membranes[27-28] suggesting an important role of this conformation in the interaction with β-cells. All these data show that the present inventors were successful in their attempts to stabilize soluble IAPP conformers. These oligomers were stable and possessed unique physical properties which distinguish them from mature amyloid structures.

Amyloid oligomers are considered toxic towards pancreatic cells and cause membrane disruption. To examine whether the newly formed conformers are indeed toxic, several complimentary methods were used. As mentioned above, several studies have showed that amyloid oligomers exhibits toxicity by forming discrete pores in biological membranes. In order to examine whether hIAPP oligomers act in the same manner, a liposomal system was used to model the cell membrane. The liposomes were packed with fluorescent salt (sodium calcein) and incubated with hIAPP oligomers (10 µM, 37° C.) or rIAPP as a negative control (FIG. 2B). Indeed, hIAPP oligomers permeabilize the liposome's membrane rapidly leading to the release of the fluorescent dye to the medium while rIAPP did not exhibit any membrane damage abilities. These results indicate that amyloid fiber formation is not necessary for membrane disruption by hIAPP and by that imply a pivotal role of oligomers as the toxic species. The toxicity of hIAPP oligomers towards cells was evaluated by 3-(4,5-dimethylthiazol-2-yl)-2,5-diphenyl tetrazolium bromide-formazan assay (MTT assay) with pancreatic RIN-m cells at different concentrations (FIG. 2A). Upon addition of hIAPP oligomers (100 nM-10 µM), MTT reduction was reduced, indicating a dose dependent decrease in cell viability. The same cells treated with rIAPP showed no such effect, again, pointing to hIAPP oligomers as the primary toxic species.

To further study this cytotoxicity, fluorescence-activated cell sorting (FACS) analysis was performed on pancreatic Rin-M cell line (FIG. 2C). Cells treated with hIAPP oligomers were found to be mostly in the early and late apoptotic phase. A clear and strong correlation between oligomer concentration and the percentage of apoptotic cells in culture could be observed (FIG. 2D). To establish the physical interaction between oligomers and β-cells; hIAPP-Hiytelfluor 488 oligomers were incubated for different periods of time and analyzed by confocal microscopy (FIG. 3). After one hour, an intensive localization of the oligomers to the cell membrane was observed which was followed by insertion of the oligomers to the cytoplasm, associated with a massive decline in cell numbers. This was readily observed after four hours. Dramatic cell morphology changes were observed after eight hours. Once again these results emphasize the cytotoxic effect of the oligomers. Thus, the effects of hIAPP oligomers were observed both in vitro and ex-vivo. The present inventors wanted to obtain further evidence regarding the relevance of these structures in a more relevant physiological surrounding. In order to achieve this, they examined whether they could identify specific antibodies that recognize hIAPP assemblies from T2D patients. To this end, total antibodies were purified from three T2D patients and three healthy individuals and their ability to detect hIAPP oligomers was compared. Dot-Blot analysis was used for quantitative assessment of the purified serum antibodies affinity to the oligomers (FIG. 4A). Antibodies from T2D patients exhibit strong recognition towards the oligomers compared to purified antibodies from healthy people serum. At 20 µg/ml antibodies purified from T2D patients showed higher binding activity than those purified from healthy individuals, lower antibody concentrations showed only binding by antibodies isolated from T2D patients (FIGS. 4A-B).

In order to verify these results, the experiment was repeated on a larger sample number. The present inventors purified antibodies from 20 individuals, 10 T2D patients and 10 healthy individuals (each group was comprised of 5 males and 5 females)—for patient details please see Table 2, herein below. Every sample was examined for hIAPP oligomer recognition at 5 μg/ml. Antibody recognition was quantitative assessed by 3,3',5,5' tetramethyl benzidine (TMB) reagent. As illustrated in FIG. 4E, T2D antibodies showed significant higher recognition properties compared to purified antibodies from healthy people serum, suggesting that T2D patients posses specific antibodies against hIAPP assemblies.

TABLE 2

| Lot Number | Age | Gender | Medications | Diagnosis Date | Lot Numbers | Gender | Age |
|---|---|---|---|---|---|---|---|
| BRH436828 | 64 | Male | ActoplusMET, ASA, Amlodipine, Benicar, Jalyn, Lipitor, Naproxen | Aug. 12, 2009 | BRH436838 | Male | 22 |
| BRH436829 | 43 | Male | ASA, Enalapril, Gabapentin, Glimipiride, Januvia, Levitra, Metformin | October 2010 | BRH436839 | Male | 32 |
| BRH436830 | 60 | Male | ASA, Aumentin, Benasepril-Hydrochlorothiazide, Cortisporin, Glimipiride, Glucovance, Hydrocortisone, Metaxalone, Promethazine-DM, Simvastatin, Tramadol, Zetia | March 2003 | BRH436840 | Male | 24 |
| BRH436831 | 55 | Male | Enalapril, Flomax, Glucotrol XL, Glyburid, Lovastatin, Metformin, Nexium, Simvastatin | July 2006 | BRH436841 | Male | 48 |
| BRH436832 | 51 | Male | ASA, Diflucan, Flonase, Glimepiride, Lantus, Levitra, Lotrisone, Metformin, Zinthromax Z-Pak | October 2009 | BRH436842 | Male | 24 |
| BRH436833 | 74 | Female | Antivert, Benicar HCT, Coreg, Glipizide, Janumet, Klor-Con M20, Lasix, Levaquin, Lidoderm, Lotrisone, Metoprolol, Naproxen, Neurontin, Nexium, Nifedipine, Pepcid, Ranexa, Robaxin, Simvastatin, Synthroid, Trazadone, Ultram ER | Dec. 8, 2010 | BRH436843 | Female | 44 |
| BRH436834 | 40 | Female | Actos, Anusol-HC, Coreg CR, Glucovance, Lotrel, Metformin | February 2009 | BRH436844 | Female | 37 |
| BRH436835 | 48 | Female | Antivert, Byetta, Enalapril, Enalapril Maleate, Glyburide, Lantus, Lovastatin, Macrobid, metformin, Metoprolol Tartrate, Vitamin D | 1998 | BRH436845 | Female | 40 |

TABLE 2-continued

| Lot Number | Age | Gender | Medications | Diagnosis Date | Lot Numbers | Gender | Age |
|---|---|---|---|---|---|---|---|
| BRH436836 | 62 | Female | ActoplusMET, Altace, Amaryl, Avandia, Gemfibrozil, Lotrisone, Simvastatin | January 2007 | BRH436846 | Female | 47 |
| BRH436837 | 69 | Female | Actos, Ambien, Atenolol, Clonazepam, Cozaar, Cymbalta, Ferrous Sulfate, Fosamax, Glucovan, Glyburide, Januvia, Lexapro, Lisinopril, Lotrisone, Metformin, Monopril, Nexium, Norvasc, Simvastatin | April 2007 | BRH436847 | Female | 28 |

To show that the conformation that T2D patient antibodies recognize is indeed the oligomeric one, PAGE analysis and Western-blot analysis was used to study the hIAPP oligomers. Positive control with commercial anti-IAPP antibody revealed monomers, dimers and trimers assemblies: negative control of purified antibodies from healthy people T2D antibodies did not exhibit any binding activities. T2D patient antibodies specifically recognized the oligomeric conformations but did not recognize the monomeric form (FIG. 4D).

The present inventors further tested whether T2D-associated antibodies can reduce the cytotoxic effect of hIAPP oligomers. In vitro cellular viability experiments were performed with pancreatic cells (FIG. 4C). As shown above, cell viability in the presence of 5 µM oligomers was reduced dramatically as monitored by MTT assay. In the presence of T2D antibodies, hIAPP oligomers toxicity was reduced in a dose dependant manner. The same analysis was preformed with non T2D antibodies and, as expected, these antibodies did not exhibit any ability to reduce the cytotoxicity of hIAPP oligomers.

The present results provide clear evidence for the role of the oligomeric species, rather than the monomeric form of IAPP, in the pathological cascade that result in cell death and loss of pancreatic β-cell mass. It is clear that the oligomeric assemblies induce apoptotic cell death probably by their interaction with the cell membrane. The ability of antibodies from human patients to interact strongly and specifically with IAPP oligomer clearly indicates that the formed assemblies as described here represent valid epitopes present in diabetic patients. Moreover, the ability of these antibodies to annul the toxic activity of the oligomeric species paves the way for new therapeutic approaches for the treatment of β-cell mass loss in the advanced stage of T2D. The newly identified and characterized species could serve as epitopes for the development of immune response in active or passive immunization. Furthermore, these species could serve as a platform for the screening and optimization of small molecules that are able to interfere with the toxic effect of oligomeric species.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Glabe, C. G. Common mechanisms of amyloid oligomer pathogenesis in degenerative disease. *Neurobiol. Aging.* 27, 570-575, (2006).
2. Selkoe, D. J. Folding proteins in fatal ways. *Nature* 426, 900-904, (2003).
3. Hardy, J. & Selkoe, D. J. The amyloid hypothesis of Alzheimer's disease: progress and problems on the road to therapeutics. *Science* 297, 353-356, (2002).
4. Snowdon, D. A. Aging and Alzheimer's disease: lessons from the Nun Study. *Gerontologist* 37, 150-156, (1997).
5. Lue, L. F. et al. Soluble amyloid beta peptide concentration as a predictor of synaptic change in Alzheimer's disease. *Am. J. Pathol.* 155, 853-862, (1999).
6. Walsh, D. M. et al. Naturally secreted oligomers of amyloid beta protein potently inhibit hippocampal long-term potentiation in vivo. *Nature* 416, 535-539, (2002).
7. Cleary, J. P. et al. Natural oligomers of the amyloid-beta protein specifically disrupt cognitive function. *Nat. Neurosci.* 8, 79-84, (2005).
8. Lesne, S. et al. A specific amyloid-beta protein assembly in the brain impairs memory. *Nature* 440, 352-357, (2006).
9. Lambert, M. P. et al. Diffusible, nonfibrillar ligands derived from Abeta1-42 are potent central nervous system neurotoxins. *Proc. Natl. Acad. Sci. USA.* 95, 6448-6453, (1998).

10. Barghorn, S. et al. Globular amyloid beta-peptide oligomer—a homogenous and stable neuropathological protein in Alzheimer's disease. *J. Neurochem.* 95, 834-847, (2005).
11. Caughey, B. & Lansbury, P. T. Protofibrils, pores, fibrils, and neurodegeneration: separating the responsible protein aggregates from the innocent bystanders. *Annu. Rev. Neurosci.* 26, 267-298, (2003).
12. Bucciantini, M. et al. Prefibrillar amyloid protein aggregates share common features of cytotoxicity. *J. Biol. Chem.* 279, 31374-31382, (2004).
13. Kautzky-Willer, A. et al. Role of islet amyloid polypeptide secretion in insulin-resistant humans. *Diabetologia* 37, 188-194, (1994).
14. Matveyenko, A. V. & Butler, P. C. Relationship between beta-cell mass and diabetes onset. *Diabetes. Obes. Metab.* 10 23-31, (2008).
15. Opie, E. L. The relation of diabetes mellitus to lesions of the pancreas, hyaline degeneration of the island of langerhans. *J. Exp. Med.* 5, 527-540., (1901).
16. Clark, A. et al. Islet amyloid, increased A-cells, reduced β-cells and exocrine fibrosis: quantitative changes in the pancreas in type 2 diabetes. *Diabetes. Res.* 9, 151-159, (1988).
17. Westermark, P. & Grimelius, L. The pancreatic islet cells in insular amyloidosis in human diabetic and non-diabetic adults. *Acta. Pathol. Microbiol. Scand.* 81, 291-300, (1973).
18. Cooper, G. J. et al. Purification and characterization of a peptide from amyloid-rich pancreases of type 2 diabetic patients. *Proc. Natl. Acad. Sci. USA.* 84, 8628-8632, (1987).
19. Westermark, P., Wernstedt, C., O'Brien, T. D., Hayden, D. W. & Johnson, K. H. Islet amyloid in type 2 human diabetes mellitus and adult diabetic cats contains a novel putative polypeptide hormone. *Am. J. Pathol.* 127, 414-417, (1987).
20. Westermark, P., Wilander, E., Westermark, G. T. & Johnson, K. H. Islet amyloid polypeptide-like immunoreactivity in the islet B cells of type 2 (non-insulin-dependent) diabetic and non-diabetic individuals. *Diabetologia* 30, 887-892, (1987).
21. Westermark, P. Fine structure of islets of Langerhans in insular amyloidosis. *Virchows. Arch. A. Pathol. Pathol. Anat.* 359, 1-18, (1973).
22. Janson, J. et al. Spontaneous diabetes mellitus in transgenic mice expressing human islet amyloid polypeptide. *Proc. Natl. Acad. Sci. USA* 93, 7283-7288, (1996).
23. Butler, A. E., Janson, J., Soeller, W. C. & Butler, P. C. Increased β-cell apoptosis prevents adaptive increase in beta-cell mass in mouse model of type 2 diabetes: evidence for role of islet amyloid formation rather than direct action of amyloid. *Diabetes* 52, 2304-2314, (2003).
24. Porat, Y., Kolusheva, S., Jelinek, R. & Gazit, E. The Human Islet Amyloid Polypeptide Forms Transient Membrane-Active Prefibrillar Assemblies. *Biochemistry* 42, 10971-10977, (2003).
25. Meier, J. J. et al. Inhibition of human IAPP fibril formation does not prevent beta-cell death: evidence for distinct actions of oligomers and fibrils of human IAPP. *Am. J. Physiol. Endocrinol. Metab.* 291, E1317-1324, (2006).
26. Patil, S. M., Xu, S., Sheftic, S. R. & Alexandrescu, A. T. Dynamic alpha-helix structure of micelle-bound human amylin. *J. Biol. Chem.* 284, 11982-11991, (2009).
27. Apostolidou, M., Jayasinghe, S. A. & Langen, R. Structure of alpha-helical membrane-bound human islet amyloid polypeptide and its implications for membrane-mediated misfolding. *J. Biol. Chem.* 283, 17205-17210, (2008).
28. Brender, J. R. et al. Amyloid fiber formation and membrane disruption are separate processes localized in two distinct regions of IAPP, the type-2-diabetes-related peptide. *J. Am. Chem. Soc.* 130, 6424-6429, (2008).
29. Wiltzius, J. J., Sievers, S. A., Sawaya, M. R. & Eisenberg, D. Atomic structures of IAPP (amylin) fusions suggest a mechanism for fibrillation and the role of insulin in the process. *Protein. Sci.* 18, 1521-1530, (2009).
30. Westermark, P., Engstrom, U., Johnson, K. H., Westermark, G. T. & Betsholtz, C. Islet amyloid polypeptide: pinpointing amino acid residues linked to amyloid fibril formation. *Proc. Natl. Acad. Sci. USA* 87, 5036-5040, (1990).

What is claimed is:

1. A composition of matter comprising isolated non-crosslinked oligomers of human islet amyloid polypeptide (IAPP) and an ionic surfactant, wherein the majority of said oligomers are dimers and/or trimers and wherein said oligomers are stable for up to 7 days.

2. The composition of matter of claim 1, wherein said ionic surfactant comprises sodium dodecyl sulfate (SDS).

3. A method of identifying an agent useful for treating diabetes, the method comprising contacting the agent with the composition of matter of claim 1, wherein a down-regulation of an amount or activity of said oligomers is indicative of an agent useful for the treatment of diabetes.

4. The method of claim 3, wherein the agent is a small molecule or an antibody.

5. The method of claim 3, wherein said contacting is effected in the presence of cells.

6. A vaccine comprising the composition of matter of claim 1 and an immunologically acceptable carrier.

7. A method of treating diabetes in a subject in need thereof, the method comprising administering to the subject an effective amount of the vaccine of claim 6, thereby treating diabetes in the subject.

* * * * *